United States Patent
Ikuta et al.

(10) Patent No.: US 11,497,382 B1
(45) Date of Patent: Nov. 15, 2022

(54) APPARATUS AND METHOD FOR ENDOSCOPIC IMAGE ORIENTATION CONTROL

(71) Applicant: CANON U.S.A., INC., Melville, NY (US)

(72) Inventors: Mitsuhiro Ikuta, Cambridge, MA (US); Anderson Thi Mach, Cambridge, MA (US); Seiji Takeuchi, Newton, MA (US); Xuri Yan, Newton, MA (US)

(73) Assignee: Canon U.S.A., Inc., Melville, NY (US)

( * ) Notice: Subject to any disclaimer, the term of this patent is extended or adjusted under 35 U.S.C. 154(b) by 42 days.

(21) Appl. No.: 17/213,832

(22) Filed: Mar. 26, 2021

Related U.S. Application Data

(60) Provisional application No. 63/015,978, filed on Apr. 27, 2020.

(51) Int. Cl.
*A61B 1/00* (2006.01)
*H04N 5/262* (2006.01)
(Continued)

(52) U.S. Cl.
CPC ...... *A61B 1/00009* (2013.01); *A61B 1/00039* (2013.01); *A61B 1/00066* (2013.01);
(Continued)

(58) Field of Classification Search
CPC ............... H04N 5/2628; H04N 5/2256; H04N 2005/2255; A61B 1/00009;
(Continued)

(56) References Cited

U.S. PATENT DOCUMENTS 6,471,637 B1 * 10/2002 Green ................ A61B 1/00045
600/137
7,134,992 B2    11/2006 Schara et al.
(Continued)

OTHER PUBLICATIONS

Lee HC, Jung CW, Kim HC. Real-time endoscopic image orientation correction system using an accelerometer and gyrosensor. PLoS One. Nov. 3, 2017;12(11):e0186691. doi: 10.1371/journal.pone. 0186691. PMID: 29099845; PMCID: PMC5669437. (Year: 2017).*
(Continued)

*Primary Examiner* — John R Schnurr
(74) *Attorney, Agent, or Firm* — Canon U.S.A., Inc., IP Division

(57) ABSTRACT

A system and method for displaying an endoscope image in a preferred orientation. An endoscope scans a sample with spectrally encoded light by rotating imaging optics inside an endoscope guide. A processor generates an image based on light returned from the sample, and rotates the image by a first angle offset value and a second angle offset value to display the rotated image in the preferred orientation. The first offset value is an angle difference between a specific direction in which the image is to be displayed on a display and a direction in which the tip of the endoscope is oriented with respect to the imaging plane. The second offset value is an angle difference between a direction of the line of scanning light projected onto a plane perpendicular to the tip and the specific direction in which the image is to be displayed.

20 Claims, 12 Drawing Sheets

(51) Int. Cl.
*H04N 5/225* (2006.01)
*A61B 1/07* (2006.01)
*A61B 90/00* (2016.01)

(52) U.S. Cl.
CPC ............ *A61B 1/00154* (2013.01); *A61B 1/07* (2013.01); *A61B 90/37* (2016.02); *H04N 5/2256* (2013.01); *H04N 5/2628* (2013.01); *A61B 2090/373* (2016.02); *H04N 2005/2255* (2013.01)

(58) Field of Classification Search
CPC ............ A61B 1/00039; A61B 1/00066; A61B 1/00154; A61B 1/07; A61B 90/37; A61B 2090/373
See application file for complete search history.

(56) References Cited

U.S. PATENT DOCUMENTS

| | | | |
|---|---|---|---|
| 7,382,949 B2* | 6/2008 | Bouma | A61B 5/0066 385/38 |
| 7,585,273 B2 | 9/2009 | Adler et al. | |
| 7,783,133 B2* | 8/2010 | Dunki-Jacobs | A61B 5/067 600/101 |
| 7,824,328 B2 | 11/2010 | Gattani et al. | |
| 7,905,827 B2 | 3/2011 | Uchiyama et al. | |
| 8,248,414 B2 | 8/2012 | Gattani et al. | |
| 9,039,608 B2* | 5/2015 | Donhowe | A61B 1/00147 600/117 |
| 9,408,257 B2 | 8/2016 | Lollar | |
| 9,561,022 B2 | 2/2017 | Sharonov | |
| 9,854,962 B2 | 1/2018 | McGrail et al. | |
| 10,261,223 B2 | 4/2019 | Tearney et al. | |
| 10,362,240 B2 | 7/2019 | Richardson et al. | |
| 10,321,810 B2 | 9/2019 | Ikuta et al. | |
| 10,401,610 B2* | 9/2019 | Ikuta | A61B 1/00172 |
| 10,895,692 B2* | 1/2021 | Yamada | G02B 6/3604 |
| 2002/0161280 A1* | 10/2002 | Chatenever | A61B 1/042 600/137 |
| 2004/0236180 A1* | 11/2004 | Uchiyama | A61B 1/041 600/114 |
| 2005/0123179 A1* | 6/2005 | Chen | G06T 3/60 382/128 |
| 2005/0154260 A1* | 7/2005 | Schara | A61B 1/04 600/173 |
| 2005/0187432 A1* | 8/2005 | Hale | A61B 5/065 600/173 |
| 2005/0228230 A1* | 10/2005 | Schara | A61B 1/042 600/173 |
| 2006/0084840 A1* | 4/2006 | Hoeg | A61B 1/042 600/117 |
| 2006/0170765 A1* | 8/2006 | Akimoto | A61B 1/0005 348/45 |
| 2008/0108870 A1 | 5/2008 | Wiita et al. | |
| 2010/0076263 A1* | 3/2010 | Tanaka | A61B 1/0051 600/109 |
| 2011/0026787 A1 | 2/2011 | Hale et al. | |
| 2014/0221749 A1* | 8/2014 | Grant | A61B 1/00096 600/109 |
| 2015/0073270 A1 | 3/2015 | Miesner et al. | |
| 2016/0192823 A1* | 7/2016 | Yasunaga | A61B 1/00066 600/109 |
| 2016/0374562 A1* | 12/2016 | Vertikov | A61B 5/0095 600/424 |
| 2018/0064396 A1* | 3/2018 | Wang | A61B 1/00009 |
| 2019/0328217 A1* | 10/2019 | Moreau | A61B 1/05 |
| 2020/0154985 A1* | 5/2020 | Ikuta | A61B 1/0623 |
| 2020/0397252 A1* | 12/2020 | Talbert | H04N 13/254 |
| 2020/0402228 A1* | 12/2020 | Talbert | H04N 5/2253 |
| 2020/0404189 A1* | 12/2020 | Talbert | A61B 1/000095 |
| 2021/0015346 A1* | 1/2021 | Kuroda | A61B 1/05 |
| 2021/0127948 A1* | 5/2021 | Pang | A61B 1/00188 |
| 2021/0267695 A1* | 9/2021 | Hazelton | A61B 1/000094 |
| 2022/0087507 A1* | 3/2022 | Yan | A61B 1/07 |
| 2022/0142462 A1* | 5/2022 | Douk | A61B 1/00172 |

OTHER PUBLICATIONS

Lee, H.C, et al., "Real-time endoscopic image orientation correction system using an accelerometer and gyrosensor", PLOS, Nov. 3, 2017, vol. 12, No. 11.

Holler, K. et al., "Endoscopic Orientation Correction", MICCAI 2009, pp. 459-466.

Ikuta, et al., "Single-beam specially encoded color imaging", Optics Letters, May 15, 2018, vol. 43, No. 10.

* cited by examiner

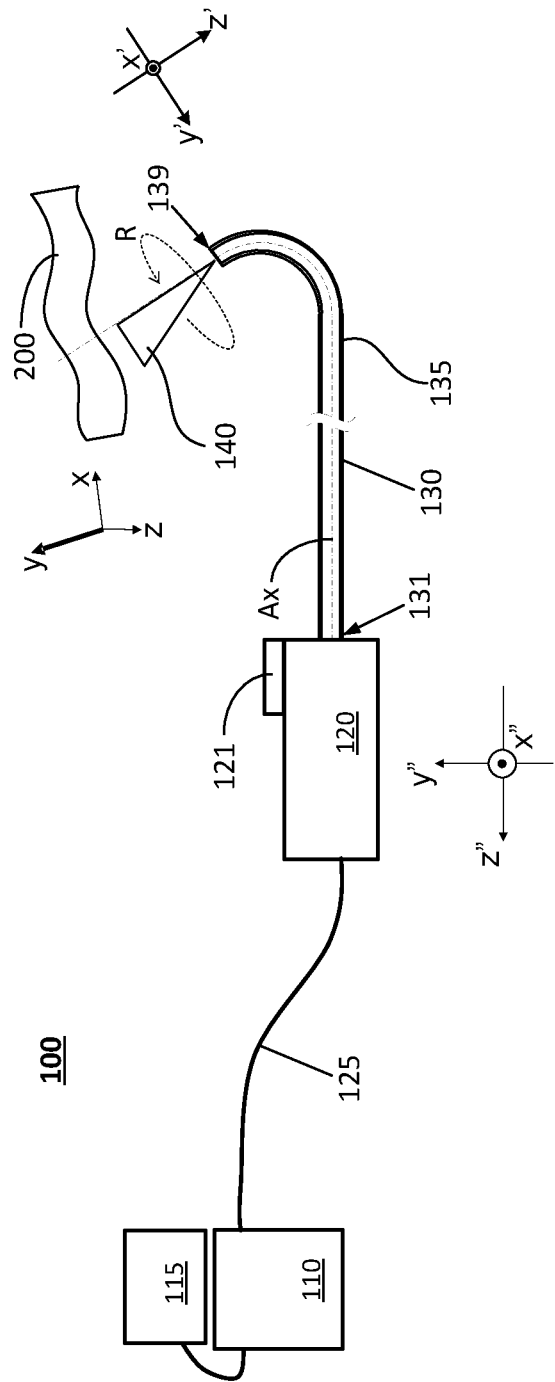

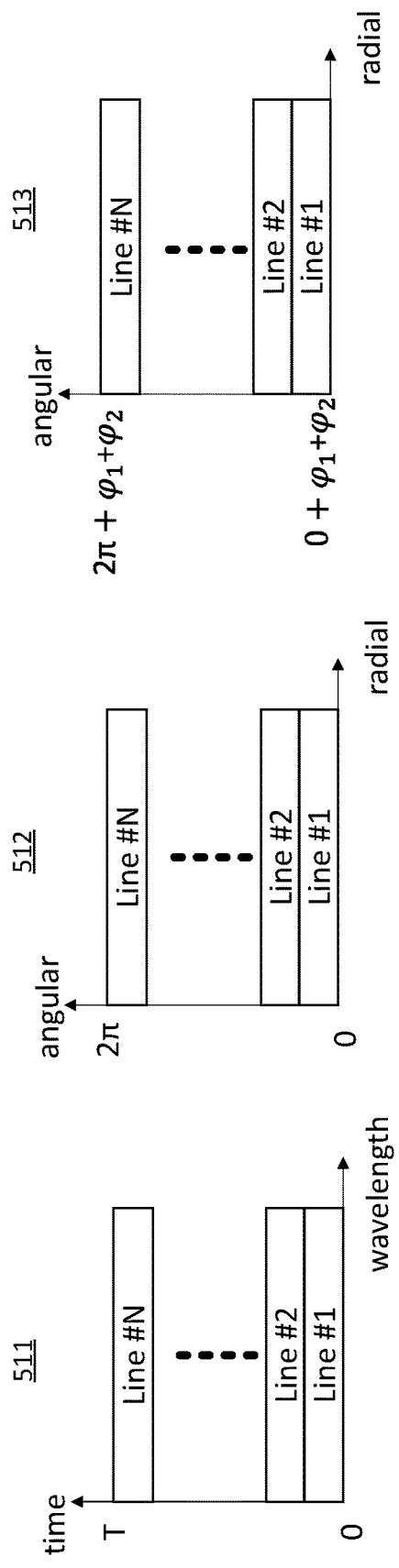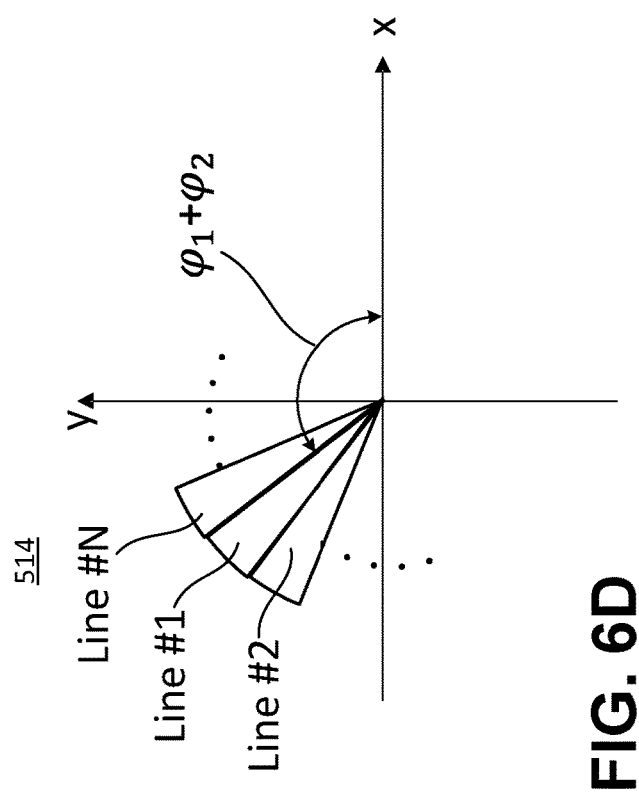
FIG. 6A  FIG. 6B  FIG. 6C  FIG. 6D

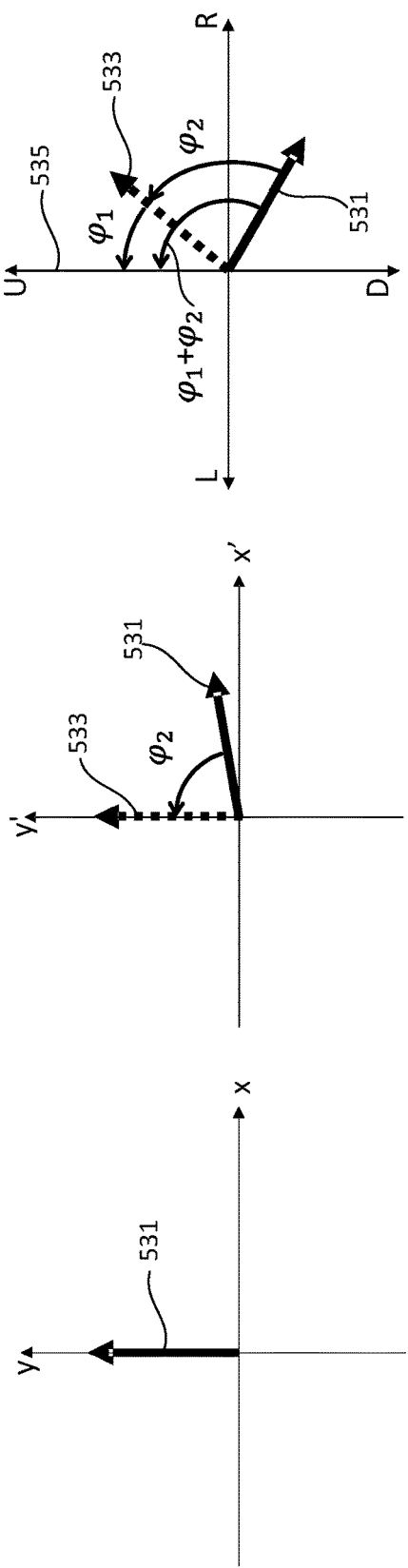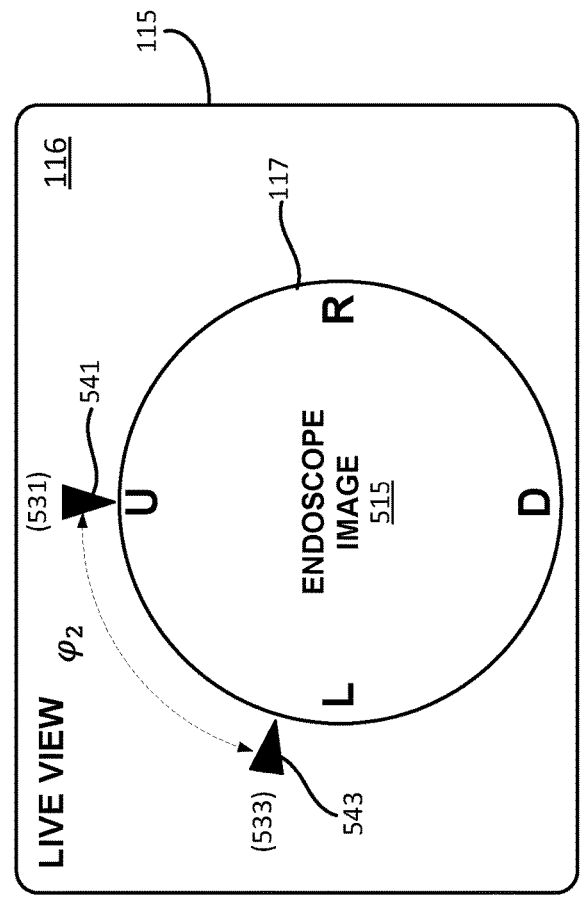
FIG. 7A
FIG. 7B
FIG. 7C
FIG. 7D (x, y, z): target space coordinate system
(x', y', z'): endoscope tip coordinate system
(x", y", z"): endoscope handle coordinate system

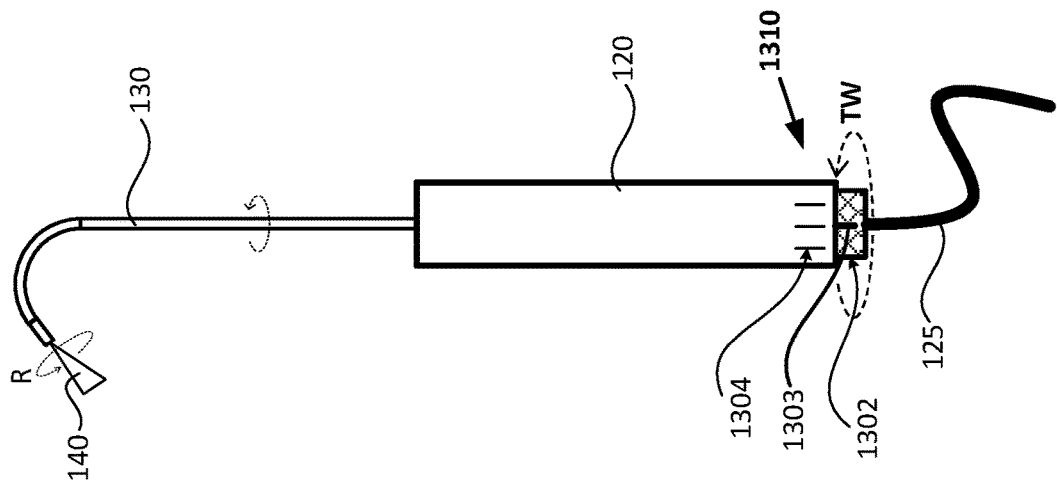
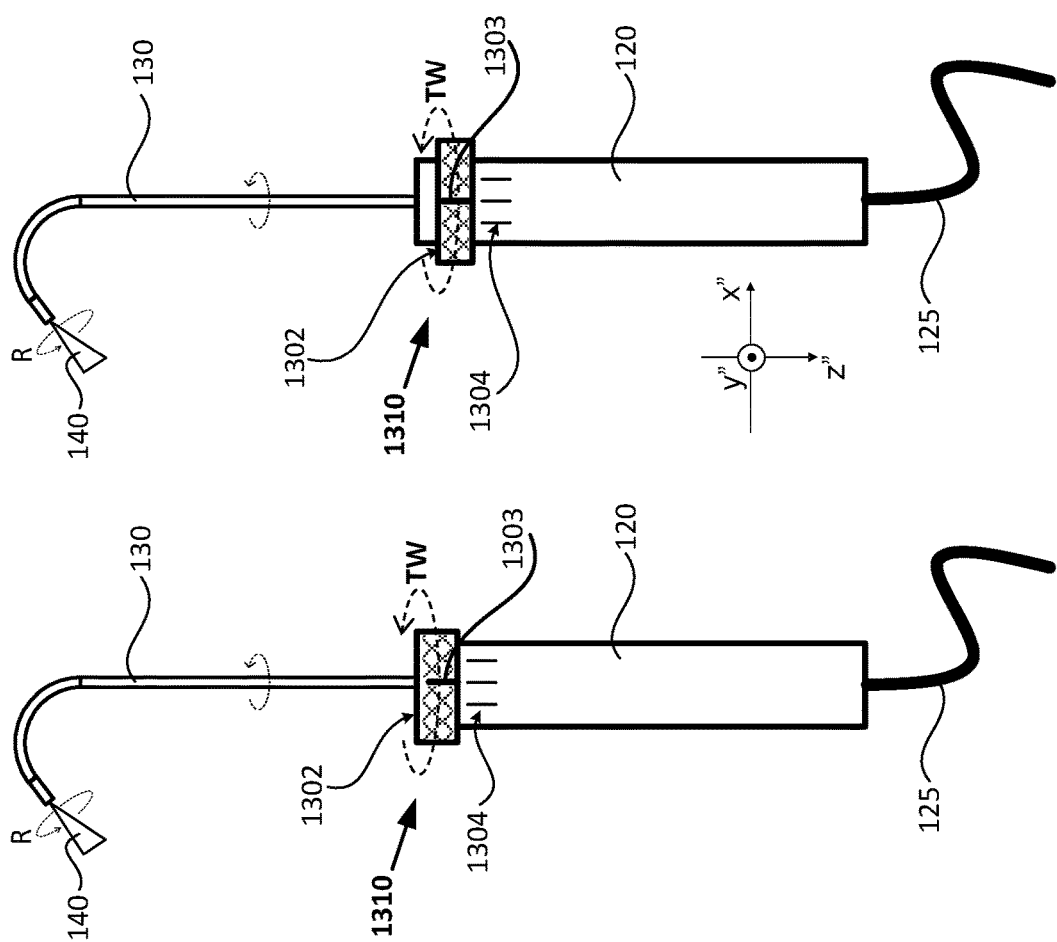
FIG. 13A  FIG. 13B  FIG. 13C

APPARATUS AND METHOD FOR ENDOSCOPIC IMAGE ORIENTATION CONTROL

CROSS-REFERENCE TO RELATED APPLICATIONS

The present application claims priority to U.S. provisional application 63/015,978 filed Apr. 27, 2020. The disclosure of the above-listed provisional application is hereby incorporated by reference in its entirety for all purposes. Priority benefit is claimed under 35 U.S.C. § 119(e).

BACKGROUND INFORMATION

Field of Disclosure

The present disclosure generally relates to optical imaging. More particularly, the disclosure exemplifies various aspects of endoscopic imaging and endoscopic image orientation control.

Description of Related Art

Medical imaging probes can be inserted through natural orifices or small incisions of a patient's body to provide detailed images from inside the patient's body while being minimally invasive to the patient's comfort. For example, video endoscopes, such as laparoscopes, gastroenteroscopes, and bronchoscopes, are commonly used to help physicians diagnose and treat patients.

FIG. 14 shows a conventional videoscope system 900. A conventional videoscope system 900 includes an endoscope probe 910, an endoscope camera 920, an image processor 930, a display 940, and a light source 950. Illumination light is delivered from the light source 950 to a sample 960 through illumination optics (e.g., an optical fiber or fiber bundle) inside, and beam directing optics at the distal end of, the endoscope probe 910. Light scattered or reflected from the sample 960 is collected by detection optics (not shown) also contained in the endoscope probe 910 and delivered to the endoscope camera 920. A two-dimensional (2D) image of the sample 960 is formed on a sensor 922 of the camera 920. The 2D image is transferred electronically to the processor 930 and processed. The processed image 962 is displayed in the display 940. The endoscope user can rotate the camera 920 and sensor 922 in a direction R with respect to the endoscope probe 910 so that the user can change the orientation of the processed image 962.

Discrepancies between spatial orientations of the videoscope image and a physician's working environment can make it difficult to appropriately interpret endoscopic images. Therefore, video endoscopes are difficult to operate, and it takes time for physicians to learn how to interpret endoscopic images. To address this difficulty, there have been several proposals directed to controlling and correcting endoscopic image orientation. Methods for controlling rotation of the displayed image include measuring the orientation of the endoscope, and then rotating the endoscopic image optically, mechanically or electronically to compensate for the orientation of the endoscope. See, for example, Lee et al., "Real-time endoscopic image orientation correction system using an accelerometer and gyrosensor", PLOS, Nov. 3, 2017. See also Höller K. et al. (2009) "Endoscopic Orientation Correction." In: Yang G Z., Hawkes D., Rueckert D., Noble A., Taylor C. (eds) Medical Image Computing and Computer-Assisted Intervention—MICCAI 2009. MICCAI 2009. Lecture Notes in Computer Science, vol 5761. Springer, Berlin, Heidelberg. See also U.S. Pat. Nos. 6,471,637, 7,585,273, 7,783,133, 7,824,328, 7,905,827, 8,248,414, 9,039,608, 9,408,257, 9,561,022, and 10362240, each of which is incorporated by reference herein for all purposes.

Spectrally encoded endoscopy (SEE) is a relatively new endoscopy application which can be used, for example, to obtain images from inside body lumens, such as from a maxillary sinus by inserting the endoscope through the natural ostium of a patient. SEE is an endoscopic technology that replaces a beam scanning device of a conventional endoscope with a miniature diffraction grating to minimize the probe size. In an SEE probe, broadband light is delivered by an optical fiber to the distal end of the probe and focused by a miniature lens. A diffraction grating, which is positioned after the miniature lens, disperses the broadband light into multiple beams with different wavelengths (colors) to generate a spectrally resolved line on the sample. Each wavelength in the line illuminates the sample at a different location, and thus encodes light reflected from tissue in a given transverse coordinate by wavelength. A line image of the tissue is acquired by analyzing the spectral frequency of light reflected from the tissue and returned by the probe. The other transverse coordinate, which is typically perpendicular to the spectrally-encoded coordinate, is scanned by rotating the SEE probe with a motor that is typically located in the endoscope handle outside of the patient.

In a rigid SEE endoscope procedure where neither the probe nor the patient is changing position during the procedure, the orientation of an SEE image is based on the rotation angle of the endoscopic probe and the spectrally-encoded light obtained through the optics contained in the probe. See, for example, U.S. patent Ser. No. 10/401,610 which is incorporated by reference herein for all purposes.

However, to access a patient's body part which is difficult to reach, for example, to access the maxillary sinus by inserting the endoscope through the natural ostium, the endoscope should be flexible and/or should have a curved shape. In such cases, endoscope users have to rotate and/or bend the endoscope guide to advance from the entry point (the nasal passage) through a tortuous path (the natural ostium) to reach the target sample (maxillary sinus) while observing a live image. In this case, to have a more intuitive procedure, endoscope users want the endoscope image orientation to be the same as the patient's orientation so that the user will not lose track of where the endoscope tip is (position) and where it is looking (orientation) while the endoscope advances through such tortuous paths towards the target location.

However, when it is difficult to rotate the whole endoscope, for example when the SEE endoscope optics is in a curved guide to access a specific location as the maxillary sinus described above, and when the movement of the curved guide is limited by the location geometry or anatomy of the patient, users cannot adjust the image orientation intuitively. Therefore, there remains a need to provide endoscope users with a solution for displaying processed endoscope images in the orientation that the user prefers.

SUMMARY OF EXEMPLARY EMBODIMENTS

According to at least one embodiment, there is provided an endoscope system comprising an endoscope contained in an endoscope guide and attached to an endoscope handle. A user holds the endoscope handle to manually advance the endoscope guide towards a target location. According to one embodiment, the endoscope can be a SEE endoscope which has illumination optics configured to provide spectrally-encoded illumination to a sample. In this case, a rotating mechanism (a motor) rotates the illumination optics inside the endoscope, while a rotation detection module tracks the rotation of the illumination optics. Endoscope detection optics detects light scattered or reflected from the sample while the illumination optics rotate inside the endoscope guide. An image processor reconstructs an image from the detected light, and displays the reconstructed image to aide the user in performing an accurate procedure. The processor is configured to obtain a first angle offset value between the rotation angle of illumination optics and guide orientation, and a second angle offset value between guide orientation and an image orientation that user prefers. The image processor rotates the image during the image reconstruction process based on one or more of the first angle offset value and the second angle offset value so that the image can be displayed in the image orientation that user prefers.

The first angle offset value is obtained by continuously monitoring the rotation of the illumination optics inside the endoscope guide using, for example, an encoder module. The second angle offset value can be obtained by a sensor which detects the tilt of the endoscope guide. The sensor may include a tilt sensor and/or an inertial sensor. The system may include a user interface, input unit, to control the tilt of the endoscope guide. The input unit may be a ring controller, a button, a touch pad, voice coil control, and the like. The second angle offset value can be continuous or discrete. In nasal endoscopy, for example, a predetermined angle offset value can be set for "left sinus" or "right sinus". When the target location (patient) is defined as arranged in an "x, y, z" coordinate system, the y-direction can be defined as the "UP" direction that the user prefers, and this direction is not related to the endoscope movement. Then, the image processor rotates the image during the image reconstruction process based on one or more of the first angle offset value and the second angle offset value so that the image can be displayed in the UP direction which is the image orientation that user prefers.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 1 shows an embodiment of an exemplary endoscopic imaging system 100.

FIG. 6A, FIG. 6B, FIG. 6C and FIG. 6D show image data processed according to the image processing flowchart of FIG. 5.

FIG. 7A, FIG. 7B, and FIG. 7C graphically explain the meaning of the first and second angle offset values 271 and 273. FIG. 7D shows an example of a screen 116 showing a reconstructed endoscope image 515 displayed in a display apparatus 115.

FIG. 13A, FIG. 13B, and FIG. 13C illustrate various examples of the endoscope guide 130 assembled with the endoscope handle 120 and configured with a user interface 1310 for endoscope guide orientation control.

DETAILED DESCRIPTION OF EXEMPLARY EMBODIMENTS

Figure 2A:
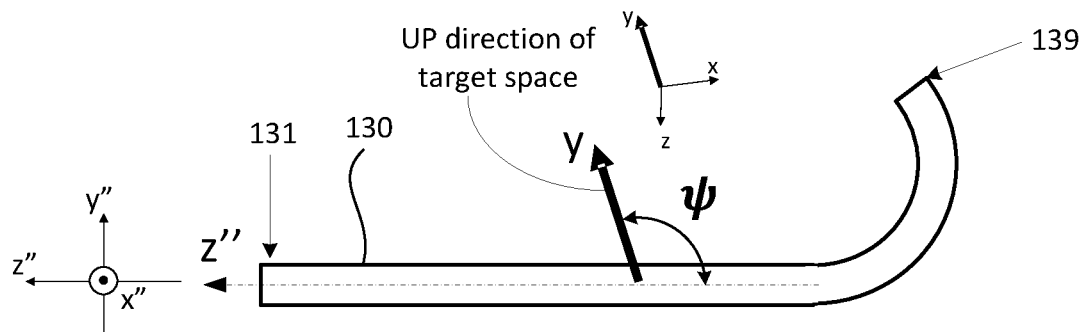
FIG. 2A, FIG. 2B, and FIG. 2C illustrate endoscope guide parameters.

The exemplary embodiments disclosed herein are based on an objective of providing an endoscope system having micron-sized fiber-optic-based endoscopic probes that can provide high quality images in an orientation that an endoscope user prefers. As used herein, micron-sized imaging probes and optical elements thereof may refer to components having physical dimensions of 1.5 millimeter (mm) or less in diameter.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to a surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ, which may be referred to as a "bodily lumen". A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

As used herein, the term "rotation" refers to the action of rotating in a circular movement around an axis or center. Rotation may include circular movement of one or more complete revolutions, or it may include a circular movement for a partial revolution. Moreover, rotation may also refer to oscillation where circular movement occurs in a back-and-forth manner for a partial or full revolution.

<FIG. 1 and FIG. 2A-2C>

FIG. 1 shows an embodiment of an exemplary endoscopic imaging system 100. The endoscope may be rigid such as those used in laparoscopy or it may be flexible so that it is capable of following the curvatures of body lumens. The endoscope may also be rigidizable and/or robotic. A rigidizable endoscope is an endoscope that has at least one section of its flexible body that can be made substantially rigid by a mechanical locking mechanism. A robotic endoscope is a flexible endoscope that has at least one section that bends under a computer controlled actuator mechanism. The endoscope may be a forward viewing endoscope; or it may be an endoscope having fixed or movable beam directing optics in the distal portion to allow off-axis viewing. The present disclosure is applicable to all types of axial, non-axial, and variable direction, flexible and rigid endoscopes.

In one embodiment, the endoscopic imaging system 100 can be an SEE endoscope imaging system. The imaging system 100 includes a console 110, a display apparatus 115, a handle 120, and an endoscope 135 enclosed in an endoscope guide 130. The console 110 and the handle 120 are operably connected to each other by a cable bundle 125. The display apparatus 115 is configured to show certain parameters of a procedure along with a processed endoscopic image acquired by the use of endoscope 135. The endoscope guide 130 is a tubular shaft having a longitudinal axis which is concentric with the endoscope axis Ax; the endoscope guide 130 encloses the endoscope 135 and extends from a proximal end 131 to a distal end 139. The endoscope guide 130 contains inside the tubular shaft, among other things, endoscope optics which may otherwise be referred to as a probe. Endoscope optics includes illumination optics and detection optics. In an exemplary SEE endoscope, the illumination optics emits a spectrally-encoded illumination light 140, and the detection optics collects light reflected and/or scattered by a sample 200. In one embodiment, the sample 200 can be a bodily lumen of a patient. The endoscope guide 130 can be rigid and straight shaft or it can be a shaft at least partially flexible and curved. The handle 120 is configured to enable a user to manually operate the endoscope guide 130. The handle 120 can have an interface 121 that indicates or selects in which direction the endoscope guide 130 is (or can be) bent or curved.

The imaging system 100 operates in a three-dimensional space defined by the Cartesian coordinate system. In FIG. 1, the y-direction in the target space coordinate system (x, y, z) is defined as the "UP" direction which is the direction that the user prefers to see in the display 115. This "UP" direction is independent from (not related to) the endoscope movement (i.e., independent from the rotation of the optical probe and/or the bending of the endoscope tip). Therefore, any direction can be set as the direction that the user prefers. The endoscope handle 120 is defined to operate in coordinate system (x", y", z") which is fixed to the endoscope handle 120. Similarly, the endoscope tip 139 is defined to operate in a coordinate system (x', y', z') which is also fixed to the tip 139 of the endoscope guide 130.

The endoscope handle coordinate system (x", y", z") and the endoscope tip coordinate system (x', y', z') vary with respect to each other mainly according to the bending angle of the endoscope tip 139. As illustrated in the various embodiments, the endoscope tip 139 is bent or bendable with respect to the longitudinal axis Ax of the endoscope guide 130. Therefore a relation between the endoscope handle coordinate system (x", y", z") and the endoscope tip coordinate system (x', y', z') is given by Equation (1), as shown below.

FIG. 2A illustrates an angle ψ defined between the "Up" direction (y-direction in the target space) and the endoscope axis Ax (z"-direction in the handle coordinate system). Specifically, FIG. 2A shows the angle ψ between the "UP" direction (y-direction in the target space coordinate system) and the endoscope axis Ax (z"-direction in the endoscope handle coordinate system). The angle ψ varies according to the pitch (tilt or inclination) and roll of the endoscope handle 120 with respect to the "UP" direction (opposite to the gravity direction) of the target space (sample 200).

Figure 2B:
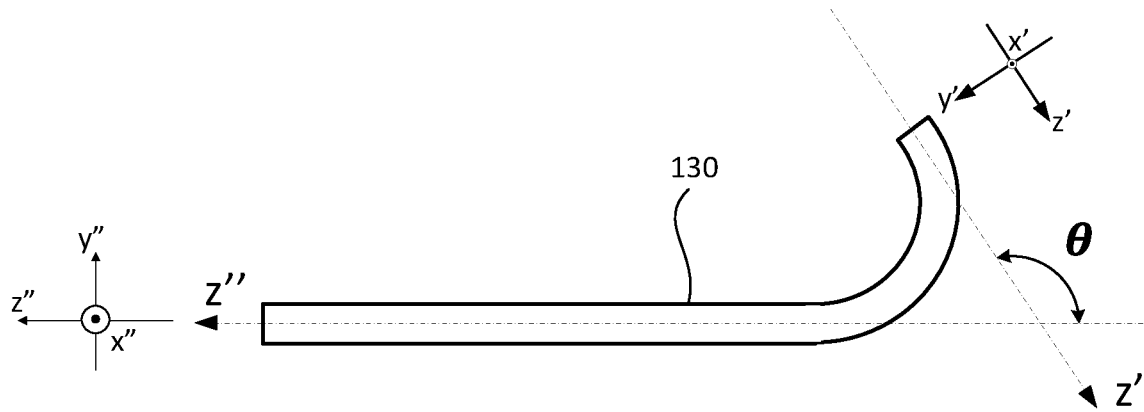

FIG. 2B shows a bending angle θ of the distal tip 139 with respect to the longitudinal axis Ax; that is, the angle θ is the angle formed between the endoscope axis Ax (in the z" direction) and the center of the endoscope at the tip 139 when the endoscope guide 130 is bent. In the case where the endoscope guide 130 is not bent at its tip, for example, in a rigid straight endoscope having a forward view, the bending angle θ would be zero.

Figure 2C:
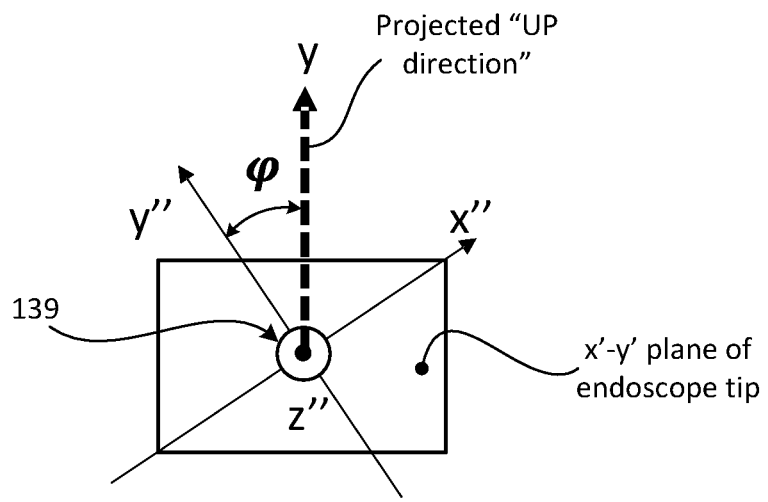

FIG. 2C shows the endoscope rotation angle φ between the endoscope handle orientation (in the x"-y" plane) and the "UP" direction projected onto the x'-y' plane (the plane of the endoscope tip 139 or the plane perpendicular to the endoscope axis).

The handle coordinate system (x", y", z") can be associated by the angle θ to the coordinate system (x', y', z') fixed to the tip 139 of the endoscope guide 130, as shown in FIG. 2C. When the tip 139 of the endoscope guide 130 is bent with respect to the longitudinal axis Ax by a bending angle θ, as shown in FIG. 2C, the relation of the endoscope tip coordinate system (x', y', z') to the endoscope handle coordinate system (x", y", z") can be represented by rotation transformation matrix given by Equation 1, as follows:

$$\begin{pmatrix} x' \\ y' \\ z' \end{pmatrix} = \begin{pmatrix} 1 & 0 & 0 \\ 0 & \cos\theta & \sin\theta \\ 0 & -\sin\theta & \cos\theta \end{pmatrix} \begin{pmatrix} x'' \\ y'' \\ z'' \end{pmatrix}. \quad \text{Eq. (1)}$$

The unit vector in the "UP" direction (y-vector in FIG. 2A) is represented by Equation 2, as follows:

$$\begin{pmatrix} x \\ y \\ z \end{pmatrix} = \begin{pmatrix} 0 \\ 1 \\ 0 \end{pmatrix} \quad \text{Eq. (2)}$$

The relation of the UP direction (unit vector of Equation 2) to the endoscope guide orientation angle Φ can be represented in the handle coordinate system (x", y", z") by Equation 3, as follows:

$$\begin{pmatrix} x'' \\ y'' \\ z'' \end{pmatrix} = \begin{pmatrix} \sin\varphi\sin\psi \\ \cos\varphi\sin\psi \\ -\cos\psi \end{pmatrix} \quad \text{Eq. (3)}$$

And the same unit vector of Equation 2 can be represented in the endoscope tip coordinate system (x', y', z') by using a rotation transformation matrix defined by Equation 4, as follows:

$$\begin{pmatrix} x' \\ y' \\ z' \end{pmatrix} = \begin{pmatrix} 1 & 0 & 0 \\ 0 & \cos\theta & \sin\theta \\ 0 & -\sin\theta & \cos\theta \end{pmatrix} \begin{pmatrix} x'' \\ y'' \\ z'' \end{pmatrix} = \begin{pmatrix} \sin\varphi\sin\psi \\ \cos\theta\cos\varphi\sin\psi - \sin\theta\cos\psi \\ -\sin\theta\cos\varphi\sin\psi - \cos\theta\cos\psi \end{pmatrix} \quad \text{Eq. (4)}$$

Therefore, to account for the effects on image orientation caused by the endoscope inclination, the endoscope roll, the bending angle θ of the endoscope tip 139 with respect to the longitudinal axis (Ax) of the endoscope guide 130, and the rotation angle φ of the endoscope optics within the endoscope guide 130, it is necessary to take into account both a first angle offset between the rotation angle of the illumination optics and the guide orientation, and a second angle offset between the guide orientation and an image orientation that a user prefers. Here, the rotation angle of the illumination optics is a value varying with time (a function of time). Therefore, for example, the first angle offset value is an angular offset between an initial value of the rotation angle and the guide orientation.

<FIG. 3>

Figure 3A:
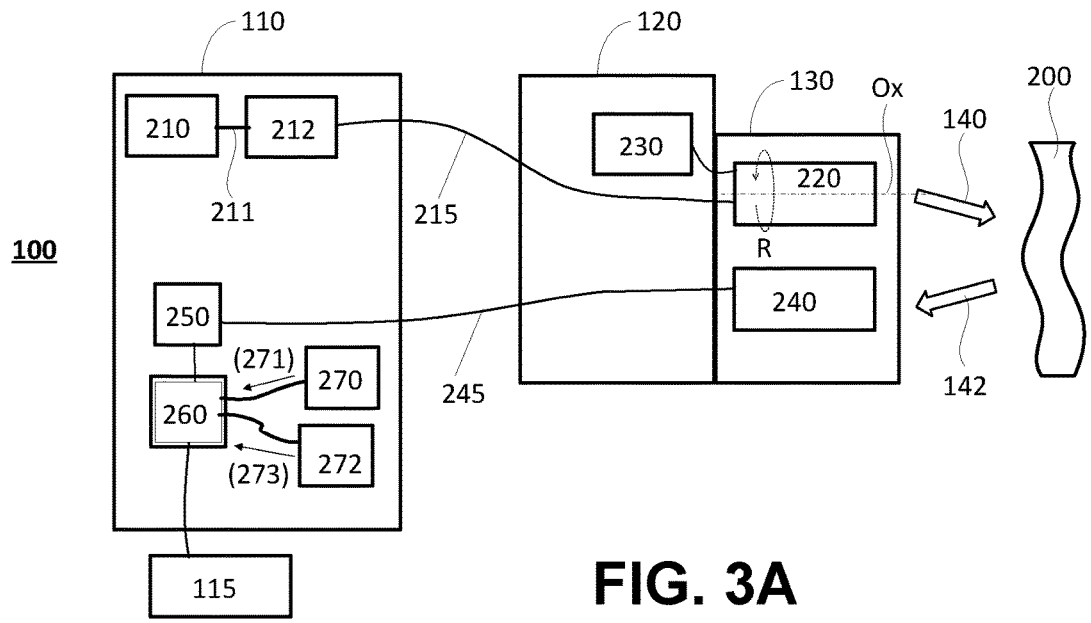
FIG. 3A shows a detailed block diagram of the endoscope imaging system 100.

FIG. 3A shows a detailed block diagram of the endoscope imaging system 100. As already described above, the imaging system 100 includes a console 110, an endoscope handle 120, and an endoscope guide 130. The endoscope guide 130 serves as a tubular conduit or lumen for, among other things, illumination optics 220 and detection optics 240. The illumination optics 220 delivers illumination light 140 to the sample 200, and the detection optics 240 collects reflected light 142 which has been reflected and/or scattered by the sample 200.

More specifically, a broadband light source 210 in the console 110 emits broadband light in a predetermined wavelength range. In one embodiment, for example, the broadband light source 210 has a wavelength range of 400-800 nanometers (nm). In this case, the broadband light source 210 generates visible light in blue, green, and red bands, where the blue band contains 400-500 nm light, the green band contains 5000-600 nm light, and the red band contains 600-800 nm. In other embodiments, the wavelengths of the broadband light source 210 can be optimized for identifying specific features such as blood, tissue, etc., and may extend into the near-infrared (NIR) region, for example 1200 nm. In an embodiment, each wavelength band may have a wavelength range that is at least about 30 nm. An embodiment may include at least three bands which would allow the SEE endoscope to produce color images. More bands may be used to acquire additional information. The broadband light source 210 can be configured by a laser device, for example, a supercontinuum laser. In other embodiments, the broadband light source 210 may include one or more of a laser, an OLED (organic light emitting diode), a LED (light emitting diode), a superluminescent diode (SLD), a halogen lamp, an incandescent lamp, and/or a fluorescent lamp. The broadband light source 210 can be any light source that provides light with a wavelength range that can be split up into at least three bands and each band can be further dispersed to provide light in different diffractive orders which is used for spectral encoding of spatial information. The broadband light source 210 may be fiber coupled or may be free-space coupled to the illumination optics 220 of the imaging system 100.

In the embodiment of FIG. 3A, the light from the broadband light source 210 is delivered to illumination optics 220 in the endoscope guide 130 through a rotary joint 212 and an illumination waveguide 215. The illumination waveguide 215 can be configured by one or more than one optical fiber, for example, by one or more than one of a single mode fiber, or a multi-mode fiber. The rotary joint 212 can be a fiber optic rotary joint (FORJ), for example, as described in U.S. Pat. No. 7,382,949 which is incorporated by reference herein in its entirety. The rotation mechanism 230 serves to rotate the illumination optics 220 so that the illumination light 140 can irradiate the target sample 200 with a rotating illumination light beam. The rotary joint 212 serves to couple light from a static fiber 211 (stator side) connected to the static light source 210 to the rotating fiber 215 (rotor side) connected to illumination optics 220. The rotation mechanism 230 may include one or more than one motor, such as a stepping motor or a micro motor having stator coils.

In one embodiment, the illumination optics 220 emits illumination light 140, which can be a spectrally-encoded illumination line directed toward the sample 200 in a forward viewing mode. When the endoscope guide 130 is configured to examine hard-to-reach target locations, which may be located not directly in a forward viewing field of view, the endoscopic probe is bent, twisted and/or rotated depending on the desired application. The illumination light 140 can be a line-shaped illumination such as that produced by spectrally encoding principles, as described in U.S. patent Ser. No. 10/321,810 and U.S. patent Ser. No. 10/401, 610 which are both incorporated by reference herein in their entirety. In other embodiments, illumination light 140 can be light or other electromagnetic radiation applicable to other applications such as, but not limited to, optical coherence tomography (OCT), near infrared fluorescence (NIRF), near infrared auto-fluorescence (NIRAF), intravascular ultrasound (IVUS), or combinations thereof.

The illumination optics 220 can be rotated around the endoscope axis Ax in a direction R by the rotation mechanism 230. Reflected light 142 from the sample 200 is collected by detection optics 240, delivered through a detection waveguide 245 to a spectrometer 250, and detected by a non-illustrated optical sensor (e.g., a line sensor). The detection waveguide 245 can be configured by one or more than one optical fibers, for example, by a ring or bundle of optical fibers arranged around the illumination optics 220. The spectrometer 250 can be connected to, or can include an optical detector, such as a line sensor to detect the light collected from the sample 200. The spectrometer 250 spectrally-decodes the reflected light 142 so that its spectral information is sent to an image processor 260. The image processor 260 processes the spectral information using image processing algorithms and reconstructs an image of the sample 200. The image of the sample 200 is thereafter output and shown in the display apparatus 115. An example of processing spectrally encoded information using image processing algorithms to reconstruct an image of a lumen sample is described by Ikuta et al., in "Single-beam spectrally encoded color imaging", Optics Letters, Vol. 43, No. 10, 15 May 2018.

As noted elsewhere in this specification, the embodiments described herein are not limited to a SEE endoscope. Therefore, the spectrometer 250 may be replaced by any other type of optical detector or sensor. For example, in an embodiment where the endoscope includes an OCT imaging probe or catheter, the image detector or sensor can be an interferometric balanced detector comprised of one or more photodetectors (photodiodes). As another example, in an embodiment where the endoscope is a videoscope, the image detector or sensor can be a miniature CMOS or CCD sensor configured to form a video image of a target area. In this case, the detector or sensor can be mounted either at the tip of the endoscope guide 130 or within the handle 120 of the endoscope system.

The image processor 260 (processing device) is operatively connected to two pre-processing modules (a first module 270 and a second module 272) to obtain a first angle offset value (271) and a second angle offset value (272), respectively. The first angle offset value 271 is an offset angle between the rotation angle of illumination optics 215 and the orientation of endoscope guide 130, and the second angle offset value (273) is an offset angle between the orientation of endoscope guide 130 and the orientation of the image to be shown on the display apparatus 115. More specifically, the image processor 260 processes the information using the two offset values 271 and 273, and reconstructs the image of the sample 200 to be output and shown in the display apparatus 115 with the orientation that the endoscope user prefers.

As used herein, a "processing device" is any device in a computer that handles the intermediate stage of processing incoming data or digital signals. For example, when a computer receives data from an input device (e.g., a keyboard), the data goes through an intermediate processing stage within the central processing unit (CPU) of the computer before the data is sent to an output device (e.g., a monitor). In that regard, the image processor 260 may contain, in addition to a CPU, other processing devices such as, for example, a field-programmable gate array (FPGA), a digital signal processor (DSP), an application specific integrated circuit (ASIC), a graphic processing unit (GPU), a system on chip (SoC), or a combination of two or more of the above, which perform some or the entire image processing and signal control of the endoscopic imaging system 100.

Figure 3B:
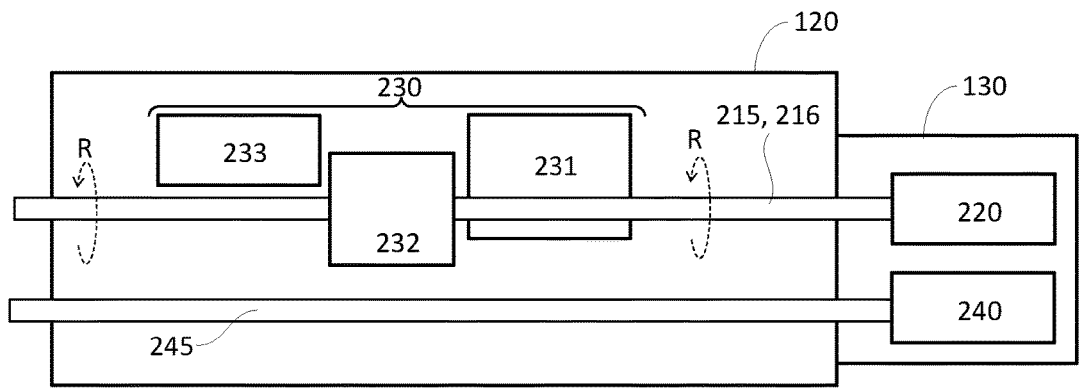
FIG. 3B shows schematic details of an embodiment of a rotation mechanism 230 included in the endoscope handle 120.

FIG. 3B shows schematic details of an embodiment of the rotation mechanism 230 included in the endoscope handle 120. As shown in FIG. 3B, the handle 120 houses therein at least the rotation mechanism 230, the illumination waveguide 215, and the detection waveguide 245. In one embodiment, the rotation mechanism 230 can use a hollow-shaft motor 231 which is configured to rotate a torque coil or drive cable 216. The illumination waveguide 215 is arranged inside the drive cable 216, and thus the hollow-shaft motor 231 rotates the drive cable 216 together with the illumination waveguide 215 in a rotation direction R. A rotation detection unit including, for example, a rotary encoder having a rotating scale or disc 232 and an encoder module 233 is provided to obtain rotation information of the drive cable 216 with respect to the endoscope guide 130. The rotating disc 232 is fixedly attached to the drive cable 216, so that the encoder module 233 can obtain the rotation information of the drive cable 216. The rotation information obtained by encoder module 233 can include at least the rotation speed, rotation direction (clockwise or counterclockwise) and/or rotation position of the drive cable 216. The rotation position of the drive cable 216 can be measured with respect to a predetermined reference point. The rotation information is sent from the encoder module 233 to console 110. At the console 110, the image processor 260 uses the rotation information provided by the encoder module 233 and the spectral information provided by the spectrometer 250 in the image reconstruction process to form and output the object image to the display apparatus 115 with the orientation that the endoscope user prefers.

In FIG. 3B, the encoder module 233 can continuously monitor the rotational position of motor 231 or rotation of the drive cable 216 with respect to a given (predetermined) reference point. For example, the encoder module 233 can include a sensor (e.g., magnetic or optical sensor) which monitors rotational position of the disc 232 by detecting its proximity to certain marks or distinguishable regions of the disc 232 while the disc rotates together with the drive cable. The encoder module 233 provides an output signal based on the actual (current) rotational position of the drive cable 216 (or motor 231) at a given point in time. The reference position (set point), which can be any reference point, can be used as a crossing point to detect the speed of rotation and/or position of the rotating drive cable 216 (including optics 220) at any given time.

More specifically, in the procedure of connecting the endoscope guide to the handle 120, a fiber connector or other structure of the endoscope probe is generally inserted in a predetermined orientation with respect to the handle. For example, the endoscope probe is connected to the handle 130 with the fiber connector aligned to a predetermined orientation (e.g., a snap lock or locking ridge of the fiber connector is inserted pointing vertically upwards, downwards, or sideways). Therefore, in order to properly monitor the rotational position (or orientation) of the endoscope probe 135 with respect to the endoscope guide 130, the encoder module 233 can use the orientation of the fiber connector as a reference point to know the rotational position at any give time. In addition, another example of a predetermined reference point can be a desired orientation in which the proximal end of the probe is inserted into the handle 130. A further example of a predetermined reference rotational position could be the motor's back-EMF zero-crossing position. In other embodiments, the predetermined rotational position may be any fixed reference point with respect to which a rotational position of the motor 130 or the drive cable 216 can established by using the encoder module 233. In this manner, as the motor 231 rotates the drive cable 216, the encoder module 233 outputs a signal indicative of the rotational position of the rotating illumination optics 220 with respect to the endoscope guide 130.

Figure 3C:
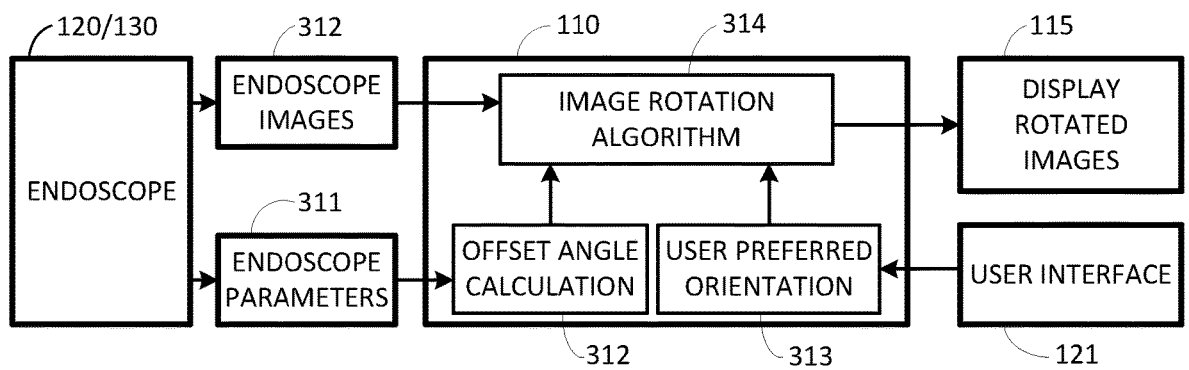
FIG. 3C illustrates a block diagram of image rotation for displaying endoscope images according to the user preferred orientation.

FIG. 3C illustrates a block diagram of image rotation for displaying endoscope images according to the user preferred orientation. As illustrated in FIG. 3C the endoscope handle 120 and endoscope guide 130 are used to acquire endoscope images 312, and, at the same time, the rotation mechanism 230 acquires or tracks endoscope parameters 311 such as, for example, endoscope handle orientation in real space with respect to the target sample, the rotation speed of the illumination optics, a predetermined reference point or predetermined reference rotational position of the illumination optics, the inclination or orientation of the endoscope guide with respect to the target location, etc. The endoscope images 312 and endoscope parameters 311 are passed to the system console 110. In addition, the console 110 receives from the user, for example via the user interface 121, information about the user preferred orientation 313, which is information indicative of the orientation in which the user prefers that the endoscope images should be displayed. The processor 260, in the system console 110, uses the endoscope parameters 311, the endoscope images 312, and the user preferred orientation 313 to perform angle offset calculation 312 and execute an image rotation algorithm 314 to display rotated endoscope images in display apparatus 115.

<FIG. 4>

Figure 4A:
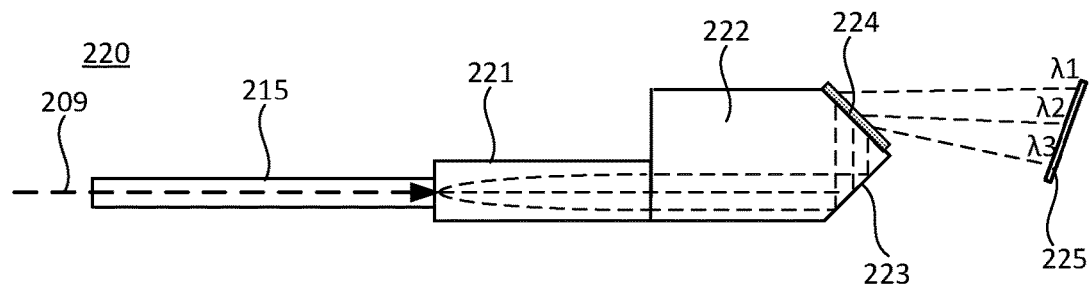
FIG. 4A and FIG. 4B show detailed schematics of an example of the endoscope illumination optics 220, the detection optics 240, and the endoscope guide 130.
Figure 4B:
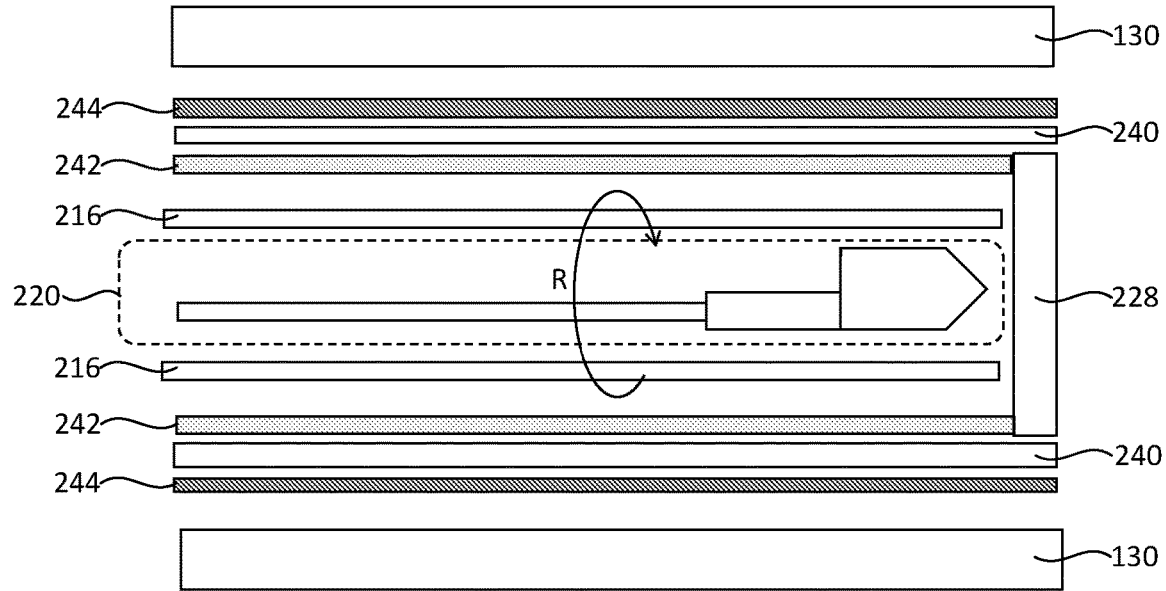

FIG. 4A and FIG. 4B show detailed schematics of the endoscope illumination optics 220, the detection optics 240, and the endoscope guide 130, according to one embodiment. In this embodiment, as mentioned above, the description is directed to an SEE endoscope, but it is not limited thereto. As shown in FIG. 4A, the illumination optics 220 includes the illumination waveguide 215 that can be a single mode or multi-mode optical fiber (a light guiding component), a focusing component 221 that can be a graded index (GRIN) lens or a ball lens, a spacer 222, and a diffractive component 224. The spacer 222 can be a transparent component having at least two surfaces configured to guide illumination light 209 provided through the illumination waveguide 215 and the focusing component 221. Specifically, the spacer 222 includes a first surface with is a reflective surface 223 and a second surface which includes the diffractive component 224 (e.g., a grating surface or prism). The spacer 222 can be made of transparent plastic, e.g., by injection molding, or can be made of glass, e.g., by glass compression molding, or it can be a piece of coreless optical fiber. The reflective surface 223 can be made by polishing a part of the spacer to satisfy total internal reflection (TIR) conditions, or it can be a mirror coated surface. The second surface containing the diffractive component 224 therein can be made by applying UV-curable resin on the second surface of the spacer 222 and stamping a master grating on the resin, by a nanoimprint technique, e.g., as described in U.S. patent Ser. No. 10/261,223 which is incorporated by reference herein in its entirety. The illumination light 209 from the illumination waveguide 215 is broadband light slightly focused by the focusing component 221 and reflected by the reflective surface 223, and thereafter diffracted by the diffractive component 224 so that a spectrally-encoded line 225 of illumination light having different wavelengths or different diffraction orders is formed over the sample 200. In this manner, the broadband light is dispersed into multiple beams of different wavelengths or different diffractive orders (λ1, λ2, λ3, etc.) to generate a spectrally resolved line on the sample. Each wavelength in the line illuminates the sample at a different location, and thus encodes light reflected from sample (e.g., tissue) in a given transverse coordinate by wavelength. The spectrometer 250 spectrally-decodes the reflected light so that its spectral information is sent to an image processor 260.

As shown in FIG. 4B, the illumination optics 220 is arranged enclosed in the inner diameter of a drive cable 216. The drive cable 216 is rotated inside of an inner sheath 242. The inner sheath 242 is surrounded by the detection optics 240 which can be a ring of detection waveguides 245 (e.g., a ring of optical fibers or a fiber bundle). The inner sheath 242 holds or supports a transparent window 228 at the distal end of the endoscope. The transparent window 228 protects the illumination optics 220 from the outside environment (e.g., fluids) which surrounds the tip of endoscope guide 130. Concentrically around the detection optics 240, there is provided an outer sheath 244 to protect the ring of optical fibers or fiber bundle of the detection optics 240. All of the foregoing components are enclosed inside (within the inner diameter) of the endoscope guide 130. As described above, the endoscope guide 130 can be rigid or flexible. At the proximal end, the endoscope guide 130 is fixedly connected to the endoscope handle 120. In operation, the endoscope guide 130 is not mechanically rotated, but the user operates the endoscope guide 130 to change the pitch, roll, and yaw (e.g., to change the scope's direction of view), by manipulating the endoscope handle 120. A tilt sensor or an inertial sensor, such as a micro electro mechanical system (MEMS) 3-axis accelerometer or an optical accelerometer tracks the movement of the endoscope as it manipulated by the user during a procedure.

Figure 5:
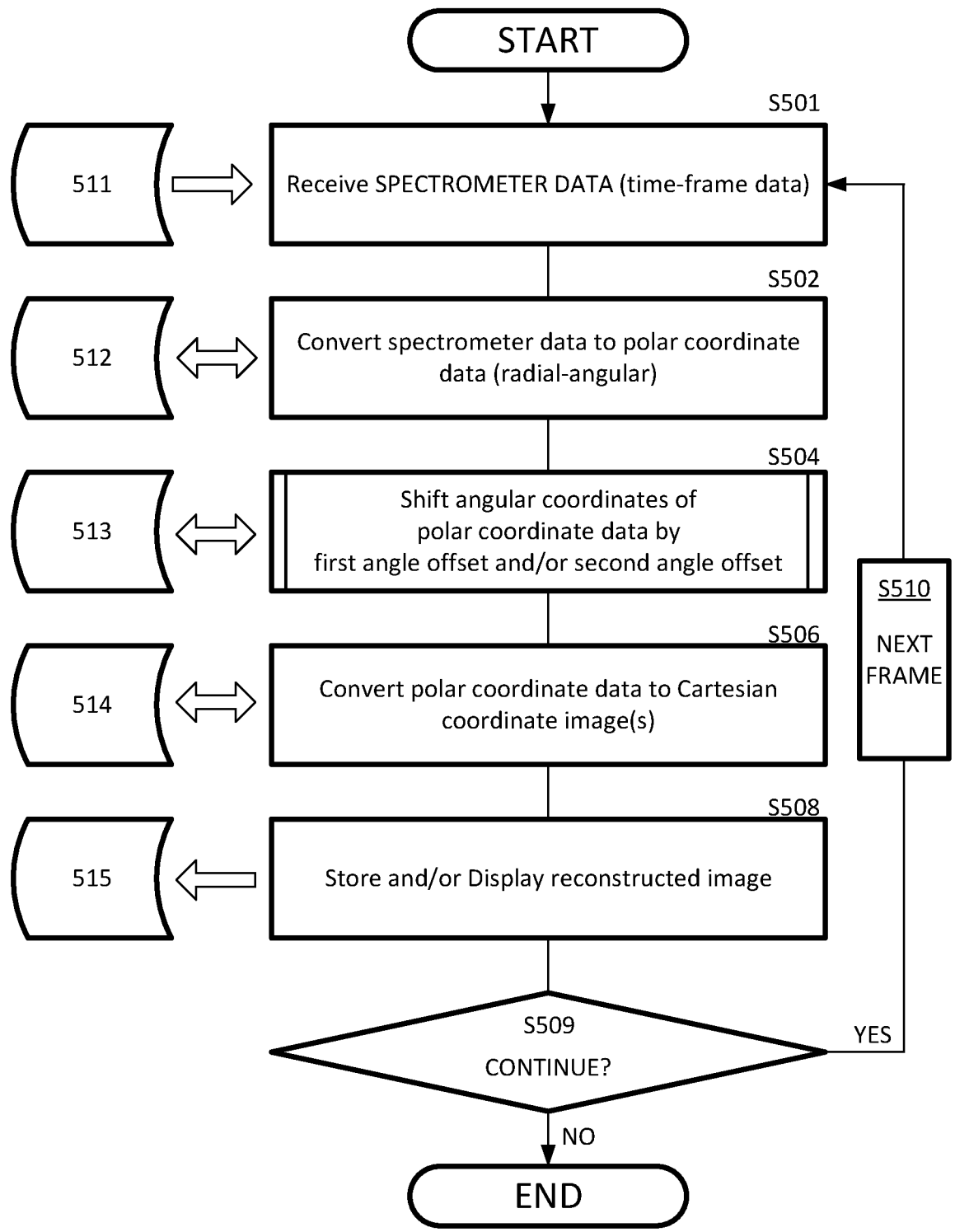
FIG. 5 shows a flowchart of image processing executed by the image processor 260.

<FIG. 5 and FIG. 6>

FIG. 5 shows a flowchart of the image processing executed by the image processor 260, and FIG. 6A, FIG. 6B, FIG. 6C and FIG. 6D show image data processed between each processing step in FIG. 5. At step S501 of FIG. 5, frame data 511 (time-frame data) is obtained from the spectrometer 250. The frame data 511 contains 1 through N spectrum lines corresponding to at least one rotation of the endoscope probe with respect to the endoscope guide 130. In FIG. 6A, T is a period of time for one rotation of the endoscope probe. Therefore, in a period from 0 to T, the system collects 1 through N lines of data. At step S502 of FIG. 5, the frame data 511 is converted to polar coordinates to form a 2D image 512 (polar coordinate data). The 2D image 512 can be one image in monochromatic imaging or it can be two or more (e.g., three) separate images in RGB color imaging.

The 2D image 512 is based on a polar coordinate system: radial and angular coordinates. FIG. 6B shows the 2D image 512 is formed of N lines in polar (radial and angular) coordinates for a full revolution. That is, at step S502, the system converts the frame data 511 into N lines of polar data acquired at angular positions from 0 to 360 degrees in one revolution of the endoscope probe. In step S503, the processor 260 calculates and/or receives a first angle offset value 271 ($\varphi_1$) and a second angle offset value 273 ($\varphi_2$). In step S504 of FIG. 5, the image processor 260 shifts the image 512 in an angular direction by $\varphi_1 + \varphi_2$, i.e., by the sum of the first and second angle offset values 271 and 273, on a line-by-line basis. In this manner, the image processor 260 converts the 2D image 512 into an angular shifted 2D image 513. FIG. 6C shows the N lines of angular-shifted data of a 2D image 513. Here $\varphi_1$ is the first angle offset value 271 and $\varphi_2$ is the second angle offset value 273 which are obtained as described in more detail below.

At the next step S506 of FIG. 5, the image processor 260 converts the angular-shifted data of image 513 to an image 514 in Cartesian coordinate system. FIG. 6D illustrates an arrangement of the N lines of the image 514 in Cartesian coordinates x and y forming a reconstructed circular image. At step S508 of FIG. 5, the processor 260 stores and/or displays the image 514 as a reconstructed image 515 in the image orientation that user prefers. At step S509, the image processor 260 determines (or prompts the user to determine) whether processing should continue. For example, at step S509, the image processor 260 may determine whether all image frame data has been processed. In the case that all image frame data has not been processed (YES at step S509), the flow process continues to step S510 to process the next frame data by repeating steps S501 through S508 until all image frame data is processed or until the endoscope user interrupts the process (NO at step S509).

In color imaging, multiple images in Cartesian coordinate system are merged to form a color image for displaying in step S508. In addition to the processing of steps S502, S504, and S506, any additional processing can be applied to the image data between those steps such as noise reduction, brightness and contrast adjustment, distortion correction (e.g., NURD correction), and gamma correction.

<FIG. 7A-FIG. 7D>

FIGS. 7A, 7B, 7C and 7D graphically explain the principles of acquiring (computing or calculating) the first and second angle offset values 271 and 273. FIG. 7D shows an example of a display screen 116 showing a reconstructed image 515 displayed in display apparatus 115. The screen 116 can show the reconstructed image 515 oriented along coordinates of up (U), down (D), left (L) and right (R) directions, as seen by a user standing in front of such screen. FIG. 7A shows a projection of a vector (arrow 531) in real space coordinates on a plane (x-y plane) of the field of view at a working distance (focusing distance) from the guide tip 139. The direction of arrow 531 in FIG. 7A is the direction (a specific direction) in real space that the endoscope user wants the image of the endoscope to be displayed in the display apparatus 115. For example, the direction of arrow 531 is the "UP" direction (with reference to the direction of gravity) in the field of view of the tip 139 that the user wants to be shown in the up (U) direction of display apparatus 115.

FIG. 7B shows the 2D plane (x'-y' plane) perpendicular to and fixed to the tip 139 (distal end) of endoscope guide 130 in the coordinate system (x', y', z') of the endoscope tip. The direction of arrow 533 in FIG. 7B is the direction for the tip 139 of the endoscope guide 130. For example, the direction of arrow 533 is the bending direction of the tip 139 of guide 130 with respect to the longitudinal axis. The direction of arrow 531 seen in FIG. 7B is a projection of the arrow 531 on the x'-y' plane fixed to the tip 139. Therefore, the direction (angle of arrow 531 with respect to arrow 533) can change when the orientation of the guide's tip 139 changes in real space. The second angle offset value 273, $\varphi_2$, is the angle representing the angular difference between the direction of arrow 531 and the direction of arrow 533 when the guide orientation moves in real space.

FIG. 7C shows a 2D coordinate system for the screen of the display apparatus 115 where an endoscope image 515 will be displayed adjusted for angle offsets values in the two systems of coordinates (i.e., the coordinate system (x', y', z') of the endoscope tip and the target space coordinate system (x, y, z) of the sample). FIG. 7C shows directions up (U), down (D), left (L), and right (R) which represent the two-dimensional plane for the screen of the display apparatus 15. Specifically, FIG. 7C shows how the directions of arrow 531 and arrow 533 would be displayed in a display apparatus 115 without the angle offset adjustment of step S504. In FIG. 7C, the direction 535 is (the UP direction) the vertical direction of the display to which the user wants to match the direction of arrow 531 by performing the angle offset adjustment process. For example, the direction 535 is the UP-direction in the coordinate system of the display apparatus 115 when the direction of arrow 531 in the target space is the "UP" direction.

The first angle offset value 271 is the value of angle $\varphi_1$ which represents an angular difference between the direction 535 (UP-direction of the display 11) and the direction of arrow 533. In turn, the direction of arrow 533 is direction for the tip 139 of the endoscope guide 130; for example, the direction of arrow 533 is the bending direction of the tip 139 with respect to the axis of endoscope guide 130. From these definitions, the direction of arrow 531 is matched to the direction 535 in display apparatus 115 when the reconstructed image is rotated by the sum of the first and second angle offset values 271 and 273, i.e., $\varphi_1 + \varphi_2$.

FIG. 7D shows an example of a screen 116 showing a reconstructed image 515 as part of a live feed (live video) displayed in display apparatus 115. In the screen 116 shown in display apparatus 115, there can be graphical indicators added to represent the angle offset values 271 and 273. For example, to show how much the second angle offset value 273, $\varphi_2$, is shifted from the direction that the user prefers, two markers 541 and 543 can be added. Here the first marker 541 is preferably always shown at the 12 o'clock direction of screen 116, which is intended to represent the "UP" U-direction in the screen. The second marker 543 can be shown around a circular guide 117 (or around the edge of reconstructed image 515). The angular difference and direction between markers 541 and 543 is used to represent in which direction the direction (of arrow 533) for the tip 139 of the guide 130 is. The direction of arrow 533 is specific direction for the tip of the guide 130, for example, the guide bending direction.

The user can turn ON/OFF the image orientation process and see whether the process is applied through the display of markers 541 and 543. For example, when the image orientation process is OFF (when the image orientation is not adjusted), the markers can disappear from the screen.

The first angle offset value 271, $\varphi_1$, can be constant as long as a relation between each spectrum line in the spectrometer image data 511 and the angle (orientation) in 2D coordinate system of the endoscope tip is static. The 2D coordinate system is perpendicular to and fixed to the tip 139 of the endoscope guide 130. A constant first angle offset value 271 for $\varphi_1$ can be realized by associating a home position of the hollow-shaft motor 231 with a specific (Mth) spectrum line in data 511, by using the rotation information of the drive cable 216 from the encoder module 233. For example, the encoder module 233 can send the signal to the system's processor 260 when the encoder detects the home position. Upon receiving an indication of the home position from the encoder, the processor 260 can identify which spectrum line (among the N lines) can be associated to the home position.

A method for the image processor 260 to obtain the first angle offset value 271 from the first module 270 can be manual or automatic. For a manual case, the console 110 can have a graphical user interface (GUI) in the screen of display apparatus 115 so that the user can manually input the first angle offset value 271 for the image processor 260. For example, the user can set the first angle offset value by adjusting the image orientation when the user holds the endoscope guide 130 so that its curve (or bending) direction matches a desired specific direction in target space such as the "UP" direction. In this case, for example, if the UP direction is parallel and opposite to the direction of gravity, the first angle offset value can be assumed to be zero ($\varphi_1=0$), or other value depending on the orientation of the guide 130 with respect to a fixed reference (e.g., the direction of gravity).

For the automatic case, the image processor 260 calculates the first angle offset value 271 by executing a software algorithm stored in module 270. For example, one method of calculating the first angel offset value 271 is obtaining an imaging reference target with an arrow that is oriented to the specific direction 533, so that image processor 260 and/or the user can identify the first angle offset value 271, $\varphi_1$. That is, the angular difference between the orientation of arrow 533 and the direction 535 (the U-direction) in the image shown in screen 116. This process can be done as a calibration step of the endoscope guide 130 prior to use of the endoscope, or it can be dynamically acquired during normal imaging operation. For example, the user can refer to a predefined test or guide chart which could have not only a pattern which specifies one direction such as an arrow but also other pattern such as a grid pattern and/or white area pattern. In this manner, the processor 260 can obtain not only the first angle offset value 271, $\varphi_1$, but also obtain distortion correction and/or white balance data.

Figure 8:
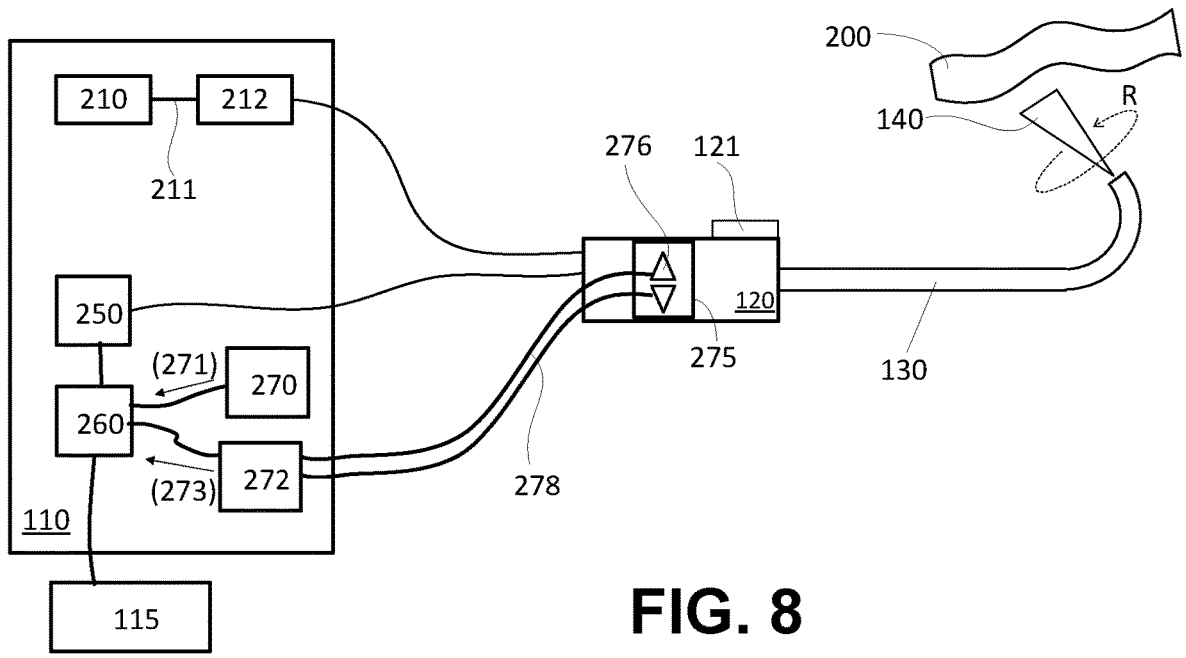
FIG. 8 illustrates an exemplary endoscopic imaging system 100 comprising a handle-based user interface 275 configured to control one or more of the first angle offset value and the second angle offset value.
Figure 9:
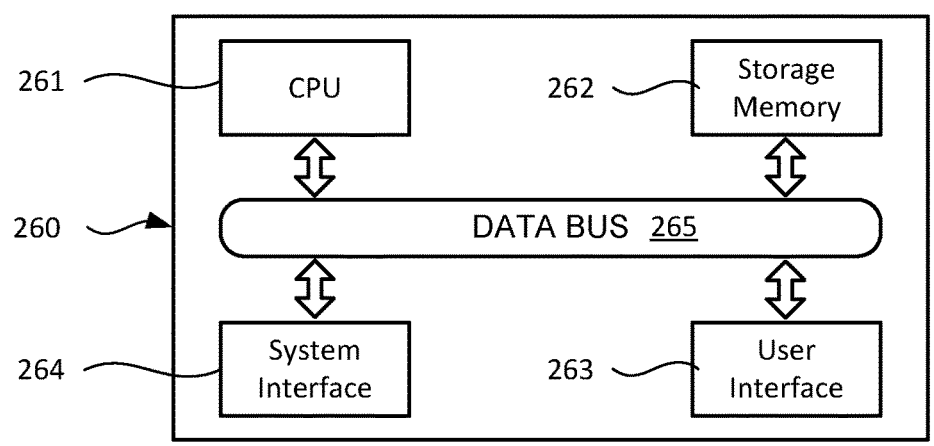
FIG. 9 shows a schematic block diagram of a processing device which implements at least the functions of image processor 260.

<FIG. 8 and FIG. 9>

FIG. 8 illustrates an exemplary endoscopic imaging system 100 comprising a user interface 275 configured to control one or more of the first angle offset value and the second angle offset value. In one embodiment, a method for the image processor 260 to obtain the second angle offset value 273 from the second module 272 can be that the user controls the value 273 of the second angle offset $\varphi_2$ through buttons 276 of an interface 275 provided in the handle 120 of the endoscope guide 130, as shown in FIG. 8. The user interface 275 can be on the handle 120, or the console 110, or on the display apparatus 115, or can be on any other device that is connected to the console 110. For example, the user interface 275 can be one or more than one button 276 on the handle 120 as shown in FIG. 8. When a button 276 is pressed by the user, it can send a command to the module 272 to increase or decrease the second angle offset value 273. The amount of increase or decrease of the second angle offset value 273 can be continuous or discrete, such as in increments of 5, or 10 or 30 or 60 or 90 or 180 degrees. In another embodiment, the user interface 275 can be a ring controller around the handle 120, a touchpad on the handle 120, or even a voice input control. In another embodiment, the user interface 275 can provide the user with means to choose a preset mode of the second angle offset value 273, $\varphi_2$.

FIG. 9 shows a schematic block diagram of a processor 260 which is implemented by, for example, a general purpose computer specifically programmed with algorithms to execute image orientation control, for example, as described with reference to FIG. 5 through 7D. The processor 260 includes or is operably attached to the display apparatus 115 for displaying the images acquired with endoscope imaging system 100. The processor 260 includes a central processing unit (CPU) 261, a storage memory (ROM/RAM) 262, a user input/output (I/O) interface 263, and a system interface 264 which are all interconnected via a data bus 265. The processor 260 can programmed to issue a command that can be transmitted to the various parts of the imaging system 100 upon receiving a user input via the user interface 263. A key board, a mouse, and/or a touch panel screen in the display apparatus 115 can be provided as part of the user interface 263.

The CPU 261 may be configured to read and perform computer-executable instructions stored in the storage memory 262. The computer-executable instructions may include program code for the performance of the methods, measurements, and/or calculations described herein. For example, CPU 261 may receive signals from spectrometer 250 to reconstruct the 2D images, and receive data from first module 270 and second module 272 to calculate the first and second angle offset values 271 and 273.

The system interface 264 provides a communication interface for input and output devices, which may include a keyboard, a display, a mouse, a printing device, a touch screen, a light pen, an optical storage device, a scanner, a microphone, a camera, a drive, communication circuit for either wired or wireless communication.

The processor 260 may contain, in addition to a CPU 261, for example, one or more of a field-programmable gate array (FPGA), a digital signal processor (DSP), an application specific integrated circuit (ASIC), a graphic processing unit (GPU), a system on chip (SoC) or combinations thereof, which performs some or the entire image processing and signaling of the endoscopy imaging system 100.

<FIG. 10>

Figure 10:
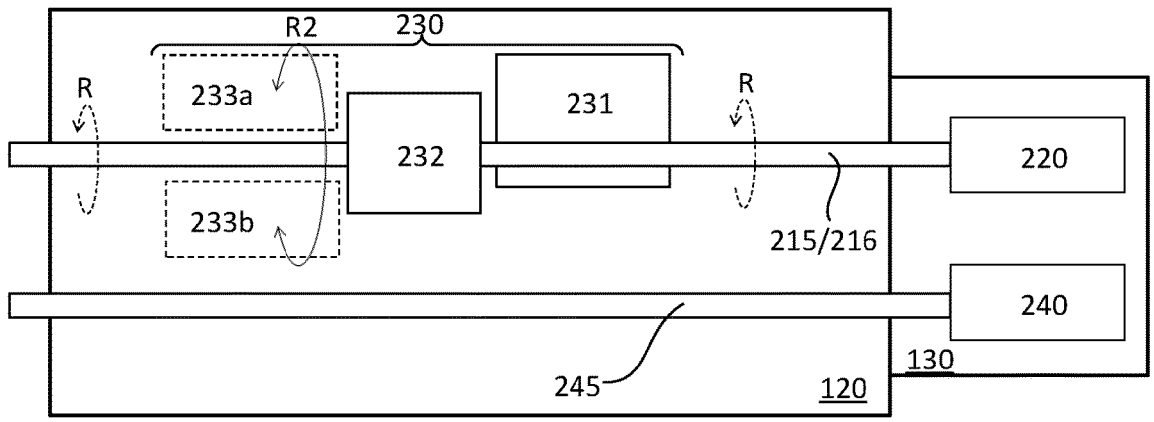
FIG. 10 shows another embodiment of the rotation mechanism 230 included in the endoscope handle 120.

FIG. 10 shows another embodiment of the rotation mechanism 230. In FIG. 10, the rotation mechanism 230 can be rotated relative to the guide 130. For example, the encoder module 233 can have rotatable portions 233a and 233b which can be rotated about the rotation axis of the motor 231 relative to the endoscope guide 130. In this case, the first angle offset value 271, the angle $\varphi_1$. representing the angle difference between the direction 535 of the display and the direction of arrow 533 (specific direction for tip of the guide 130) in FIG. 7C will be shifted; but if the value 271 is not updated to the image processor 260, the shift amount is corresponding to the value of the second angle offset 273, i.e., the value of $\varphi_2$. The user can control the second angle offset value 273 indirectly by rotating the rotatable portions 233a and 233b of encoder module 233 as shown by R2. Rotating the rotatable portions 233a and 233b of encoder module 233 by R2 means changing the home position discussed above, which is not the same as the continuous rotation R of disc 232 attached to drive cable 216. If the home position is changed but according a change for the first angle offset value 271, $\varphi_1$, is not applied to the image processor, this encoder rotation changes the angle between the direction of arrow 531 and the direction 535, by ($\varphi_1+\varphi_2$). That means this rotation is equivalent to changing $\varphi_2$ indirectly.

<FIG. 11>

Figure 11:
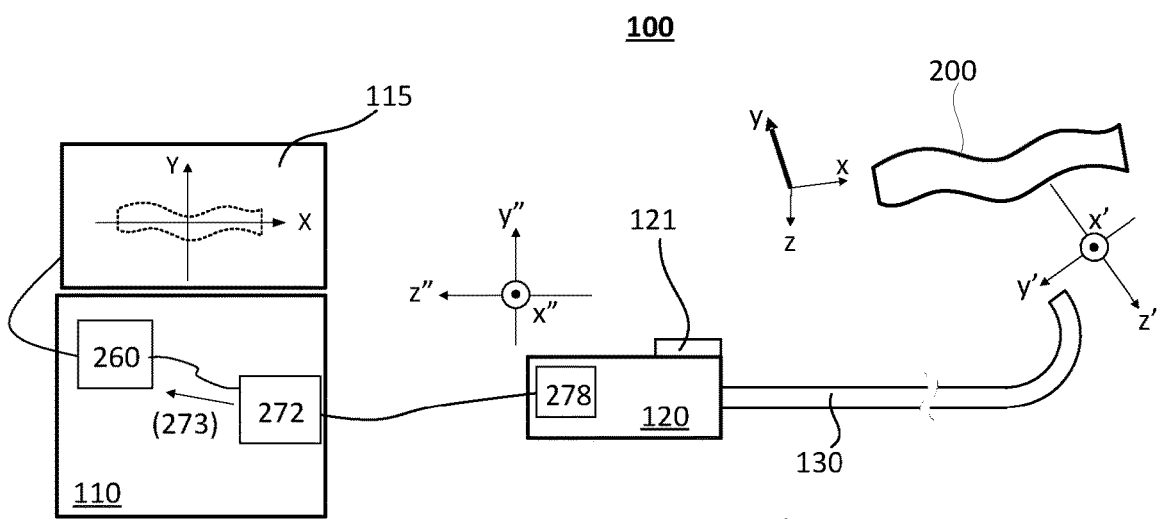
FIG. 11 illustrates an exemplary endoscopic imaging system 100 comprising endoscope orientation detection unit 278 provided in the endoscope handle 120.

In another embodiment, the second angle offset value 273, $\varphi_2$, can be determined automatically based on the endoscope orientation detection unit 278 as shown in FIG. 11. The orientation detection unit 278 can be in the handle 120. The detection unit 278 can be a tilt sensor or an inertial sensor, such as a MEMS 3-axis accelerometer or an optical accelerometer. The orientation detection unit 278 can detect the endoscope orientation so that it can identify the relation between the target space coordinate system (x, y, z) and the endoscope handle coordinate system (x", y", z"). The y-direction in the target space coordinate system (x, y, z) is defined as the "UP" direction which the user prefers. This "UP" direction is independent from (not related to) the endoscope movement. Therefore, any direction can be set as the direction that the user prefers.

The orientation detection unit 278 can identify and record the angle $\psi$ between the "Up" direction (y) in real space and the endoscope handle axis (z") as shown in FIG. 2A. The orientation detection unit 278 can identify and record the endoscope rotation angle $\varphi$ between the endoscope handle orientation (with respect to the x"-y" plane) and the "Up" direction (y-direction of the real space) projected on the x"-y" plane as shown in FIG. 2C. For example, the detection unit 278 can be a 3-axis accelerometer, and it can identify the direction of the gravity (y"-direction) in terms of the handle coordinate system (x", y", z"), which includes angles $\psi$ and $\varphi$.

Equation 4 described above defines a vector which corresponds to the vector of arrow 531 projected onto the x'-y' plane and displayed on screen 116, as shown in FIG. 7C.

Therefore, solving Equation 4 for angle $\varphi$, the second angle offset value 273, $\varphi_2$, can be found from Equation 5, as follows:

$$\varphi_2 = -\text{sign}(\sin\varphi\sin\psi)\arccos\left(\frac{\cos\theta\cos\varphi\sin\psi - \sin\theta\cos\psi}{\sqrt{(\sin\varphi\sin\psi)^2 + (\cos\theta\cos\varphi\sin\psi - \sin\theta\cos\psi)^2}}\right) \quad \text{Eq. (5)}$$

where angle ψ and angle θ are defined above, and B is the guide bending angle.

The second module 272 can calculate the second angel offset value 273, $\varphi_2$, from the information provided by the detection unit 278. Specifically, once angles are ψ and φ are identified by the detection unit 278, as described above; then the second angle offset value 273 can be calculated by the processor 260 from Equation 5. Then, the image processor 260 can correct the orientation of the reconstructed image to show the reconstructed image on the display apparatus 115 in the orientation that the user prefers.

<FIG. 12>

Figure 12A:
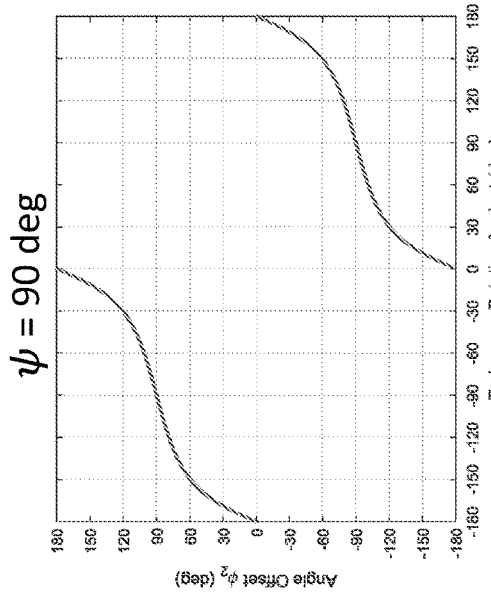
FIG. 12A, FIG. 12B, FIG. 12C, and FIG. 12D show examples of a relation between angle offset values $\varphi$ and $\varphi_2$ for different values $\psi$ when the guide bending angle $\theta$ is fixed at a predetermined value.
Figure 12B:
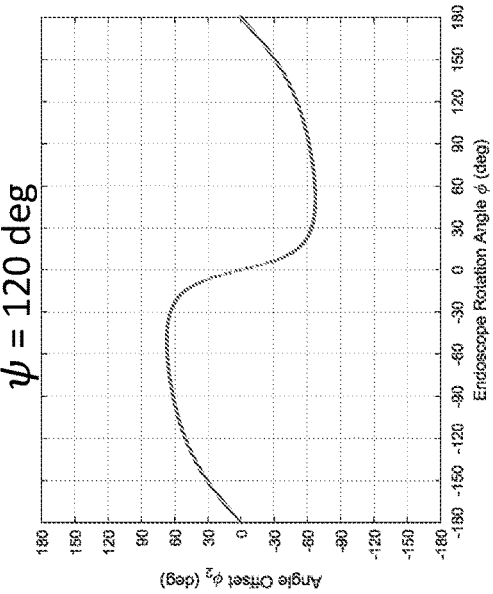
Figure 12C:
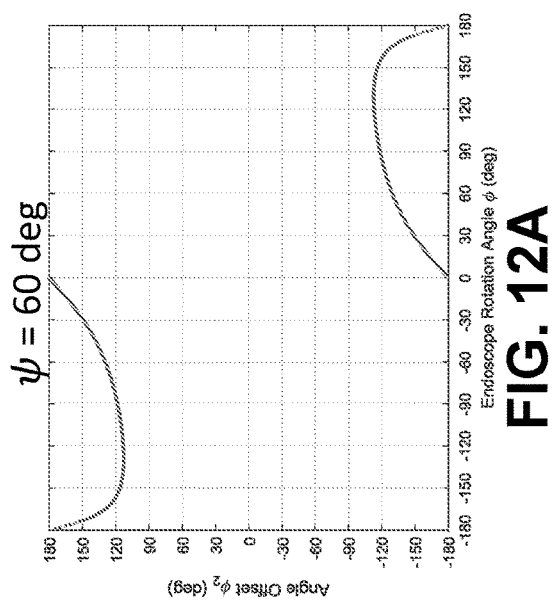
Figure 12D:
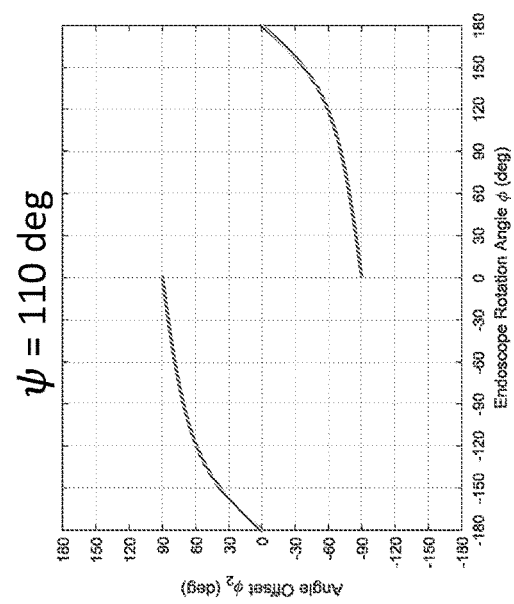
Figure 14:
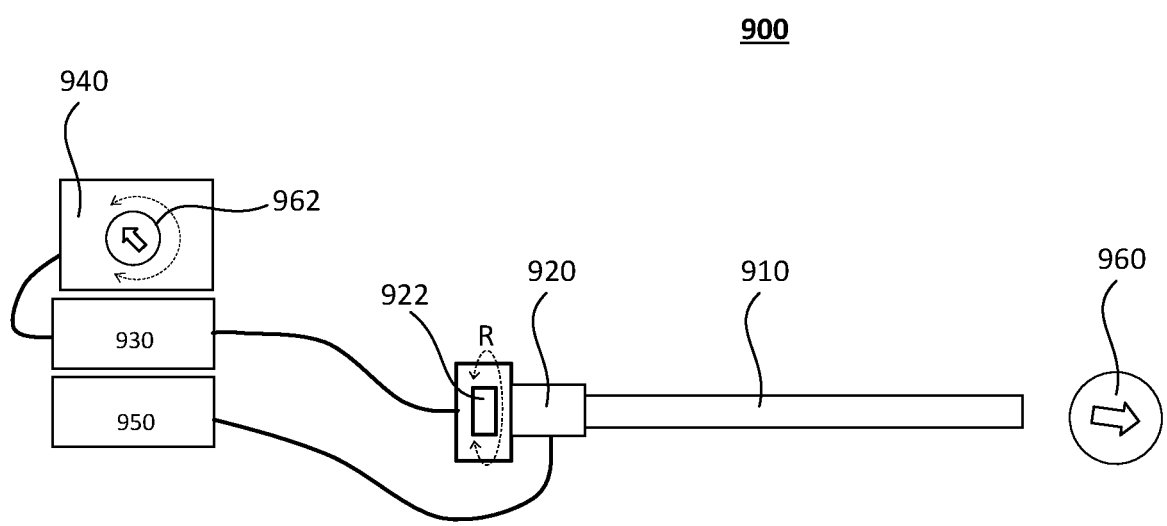
FIG. 14 shows a conventional videoscope system 900.

FIGS. 12A, 12B, 12C, and 12D show examples of the relation between φ and $\varphi_2$ for different values of ψ when the guide bending angle θ is fixed at a predetermined value. For example, when the guide bending angle θ is fixed at 110 degrees, the second angel offset value 273 of $\varphi_2$ is calculated for several ψ values as shown in FIG. 12A (for 60 degrees), FIG. 12B (for 90 degrees), FIG. 12C (for 110 degrees), and FIG. 12D (for 120 degrees). These results show that a relation between φ and $\varphi_2$ varies when ψ values change.

<FIG. 13>

FIG. 13A, FIG. 13B, and FIG. 13C illustrate various examples of the endoscope guide 130 assembled with the endoscope handle 120 and configured with a user interface 1310 for endoscope guide orientation control. FIG. 13A and FIG. 13B shows a user interface 1310 at or near the distal portion of the handle 120. The interface 1310 includes a ring dial 1302, a moving marker 1303, and an orientation indicator 1304. The endoscope guide 130 and ring dial 1302 are configured to rotate together relative to the endoscope handle 120. The moving marker 1303 moves in either clockwise or counterclockwise direction TW (by a twisting force) relative to fixed markers of the orientation indicator 1304 formed on the surface of handle 120. The markers of the orientation indicator 1304 can be printed linear markers or LED linear markers or any other type of indicators arranged at incremental discrete amounts (e.g., in degrees) of rotation.

In FIG. 13A, the interface 1310 is a knurled ring coupled (mounted or connected or attached) directly to endoscope guide 130. In FIG. 13B, the interface 1310 is a knurled ring mounted and fixed on the handle 120. Here, the ring dial 1302 rotates in a clockwise or counter clockwise direction TW relatively to the guide 130 and/or handle 120 to set an angle for the guide orientation. FIG. 13C shows a user interface 1310 in a shape of a knurled ring arranged at the proximal portion of the handle 120. In FIG. 13C, the interface 1310 is mounted and fixed to the proximal end of the handle 120, and the ring dial 1302 rotates relatively to the guide 130 and/or handle 120 to set and indicate an angle for guide orientation. The ring dial 1302 can have a gripping surface such as knurled surface for facilitating accurate control of guide orientation.

In FIG. 13A-13C, the orientation indicator 1304 can also work as a reference sensor (e.g., implemented as a Hall-effect sensor) for detecting the user preferred orientation of the endoscope guide. The detected information about the orientation of the guide 130 is sent to the console 110 via the cable bundle 125, so that processor 260 can use the information to rotate the image based on the configuration information.

Those skilled in the art will recognize that a user interface 1310 for endoscope guide orientation control can be implemented in several ways. The input can be manual input or automatic input. Manual input is manually controlled by the user. In this case, the location for guide orientation control may include the whole handle 120 as the controller, or may include only a portion of the handle 120, for example, the ring dial 1302 described in FIG. 13A-13C, or a one-thumb controlled pair of buttons as described and shown in reference to FIG. 8. Automatic input may include an acceleration sensor (accelerometer) to detect gravity or inertial movement such as described in reference to FIG. 11.

A notable difference between known conventional techniques and the techniques disclosed in the present disclosure is that that there are two angle offsets (to be considered) between the raw data and the orientation-corrected image. The first angle offset disclosed herein does not appear in conventional videoscopes, since the optics in conventional endoscopes typically are not rotating inside the endoscope guide. Moreover, conventional endoscopes typically are not concerned with effects of spectrally encoded illumination light on image orientation. Therefore, the embodiments disclosed herein are particularly advantageous to correcting image orientation in SEE endoscopy, but can be applied to any imaging technique where the imaging optics are rotated inside the endoscope guide, and endoscope roll, endoscope pitch, and endoscope viewing direction are factored into the effect of the rotating optics. In the flowchart in FIG. 5 of the present disclosure, step S504 is particularly related to the point of shifting angular values of polar coordinate data by the first angle offset value and the second angle offset value to account for image guide orientation, rotation of imaging optics, and endoscope roll, pitch, and viewing direction. The various embodiments have described in detail how to obtain (or calculate) the two angle offset values, and how to use these offset values to display the resulting image in the image orientation that the user prefers.

Software Related Disclosure for Image Processor 260

Embodiment(s) of the present disclosure can be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

According to the present disclosure, the image orientation of a reconstructed image can be changed relative to the endoscope guide orientation in a way the user can see the preferred up direction directed upward in the display. The endoscope system and method described herein can obtain a first angle offset between the rotation angle of illumination optics and the endoscope guide orientation, and a second angle offset between the guide orientation and an image orientation that a user prefers. An image processor rotates the image during the image reconstruction process based on one or more of the first angle offset and the second angle offset so that a display can show the reconstructed image in the orientation that the user prefers.

The several embodiments of the present disclosure are summarize below according to the following aspects:

Aspect 1: An endoscope imaging system (100), comprising: an endoscope (135); and an endoscope guide (130) having a proximal portion and a distal portion with a distal tip configured to provide guide orientation for the endoscope; the endoscope comprising: illumination optics (220) at least partially arranged within the endoscope guide (130) and configured to irradiate an imaging plane with a scanning illumination light (140); a rotation mechanism (230) configured to rotate the illumination optics (220) inside the endoscope guide (130); detection optics (240, 250) which detects light returned from the imaging plane; and a processor (260) in cooperation with at least the detection optics and the rotation mechanism, the processor configured to: obtain a first angle offset value ($\varphi_1$) which is an angle difference between a first direction (535) and a second direction (533), wherein the first direction (535) is a specific direction in a display plane and the second direction (533) is a direction in which the distal tip of the endoscope guide is oriented with respect to the imaging plane; obtain a second angle offset value ($\varphi_2$) which is an angle difference between a third direction (531) and the second direction (533), wherein the third direction (531) is a direction of a line of scanning light incident on the imaging plane, projected onto a plane perpendicular to the distal end (139), and which is to be displayed aligned with the first direction (535); generate an image (514) based the detected light obtained during rotation of the imaging optics, wherein the processor rotates the generated image based on one or more of the first angle offset value and the second angle offset value, such that the rotated image is oriented in the first direction which is the image orientation that the user prefers.

Aspect 2: The system according to aspect 1, further comprising: a display device (115) configured to display the image in the image orientation that the user prefers.

Aspect 3: The system according to aspect 2, wherein the image orientation that the user prefers is the "UP" direction which is a direction opposite to the gravity direction.

Aspect 4: The system according to aspect 1, wherein the image orientation that the user prefers is not related to the endoscope movement or orientation of the endoscope guide.

Aspect 5: The system according to aspect 1, wherein the processor obtains the second angle offset value ($\varphi_2$) by calculating a difference between the third direction (531) and the second direction (533) which is a bending direction for the distal tip (139) of the endoscope guide (130).

Aspect 6: The system according to aspect 1, wherein the processor obtains the first angle offset value ($\varphi_1$) by calculating an angular difference between an initial value of the rotation angle of the illumination optics and the orientation of the endoscope guide.

Aspect 7: The system according to aspect 1, wherein the distal portion of the endoscope guide is bent or curved at an angle $\theta$ with respect to a longitudinal axis (Ax) of the proximal portion.

Aspect 8: The system according to aspect 7, further comprising an endoscope handle (120) attached at the proximal end of the endoscope guide, wherein the rotation mechanism is provided in the endoscope handle, and wherein the rotation mechanism rotates the illumination optics inside a tubular body of the endoscope guide without rotating the endoscope guide.

Aspect 9: The system according to aspect 7, further comprising an orientation detection unit (278) arranged in the endoscope handle, wherein the orientation detection unit (278) is configured to determine an orientation angle $\psi$ between an "Up" direction of the imaging plane and the endoscope handle direction with respect to the imaging plane, and determine a rotation angle $\varphi$ between the endoscope handle orientation and the "Up" direction of the imaging plane projected on a plane perpendicular to the distal portion of the endoscope guide and fixed to the distal tip (139) of the endoscope guide.

Aspect 10: The system according to aspect 1, wherein the rotation mechanism (230) includes a hallow shaft motor (231) configured to rotate the illumination optics inside the endoscope guide, and a rotation sensor (233) configured to detect a rotation angle of the illumination optics with respect to the endoscope guide.

Aspect 11: An endoscope imaging system, comprising: an endoscope guide (130) having a longitudinal axis (Ax) and extending from a proximal end (131) to a distal end (139), wherein the distal end is bendable with respect to the longitudinal axis to provide a guide orientation; an optical probe (220) disposed within the endoscope guide (130) substantially along the longitudinal axis, and configured to scan an imaging plane with a line of spectrally-encoded illumination light (140); a rotation mechanism (230) configured to rotate the optical probe (220) inside the tubular shaft (130); detection optics (240, 250) configured to detect light returned from the imaging plane; a rotation sensor (233) configured to provide a first signal for use in determining a rotational angle of the optical probe (220) with respect to the endoscope guide; and a processor (260) configured to: obtain a first angle offset value ($\varphi_1$) which is an angle difference between a first direction (535) and a second direction (533), wherein the first direction (535) is a specific direction in a display plane and the second direction (533) is a direction in which the distal tip of the endoscope guide is oriented with respect to the imaging plane; obtain a second angle offset value ($\varphi_2$) which is an angle difference between a third direction (531) and the second direction (533), wherein the third direction (531) is a direction of a line of scanning light incident on the imaging plane, projected onto a plane perpendicular to the distal end (139), and which is to be displayed aligned with the first direction (535); reconstruct an image of the imaging plane based on the detected light; and perform rotational transformations upon the reconstructed image based on the first angle offset value and the second angle offset value, such that the rotationally transformed image can be displayed oriented in an image orientation that the user prefers.

Aspect 12: The system according to aspect 11, wherein the first angle offset value (271) is an angular difference between the rotation angle of illumination optics and guide orientation; wherein the first angle offset value (271) is the angle representing the angle difference between the direction (535) of the orientation that the user prefers and a direction (533) of the tip of the endoscope guide.

Aspect 13: The system according to aspect 11, wherein the first angle offset (271) is constant as long as relation is static between each spectrum line in data (511) and an angle in a plane perpendicular to and fixed to the tip (139) of the endoscope guide (130).

Aspect 14: The system according to aspect 11, wherein the processor is further configured to display a plurality of markers to show how much the second angle offset value is, wherein the plurality of markers (541 and 543) are added around an edge (117) of the reconstructed image (515)

Aspect 15. The system according to aspect 11, wherein the second angle offset value (273) is the angle representing an angular difference between the UP direction (531) in the imaging plane that the user wants to be shown in the display and the direction (533) for the tip of the endoscope guide (guide orientation).

Aspect 16. The system according to aspect 11, wherein the system further includes, a console (110), and a handle (120) rigidly connected to the endoscope guide (130).

Aspect 17. The system according to aspect 11, wherein the system further comprising a user interface (275) provided on the handle (120), or on the console (110), or on any another device that is connected to the console (110); and wherein the user interface (275) includes one or multiple buttons (276) on the handle (120), and wherein, when the one or multiple buttons are pressed by the user, the processor sends a command to increase or decrease the second angle offset value (273), and wherein the amount of the increasing or decreasing is continuous or discrete in increments of 30 or 60 or 90 or 180 degrees.

Aspect 18. The system according to aspect 11, wherein the user interface (275) includes a ring controller around the handle (120), or a touchpad on the handle 120, and wherein the user interface (275) enables the user to choose a preset mode of the second angle offset value (273).

Aspect 19. The system according to aspect 11, wherein processor (260) determines the second angle offset value automatically based on the endoscope orientation detection unit (278), wherein the orientation detection unit (278) includes a tilt sensor or an inertial sensor, wherein the orientation detection unit detects the endoscope orientation so that the processor (206) can identify a relation between a target space coordinate system (x, y, z) and an endoscope handle coordinate system (x", y", z"), and wherein the y-direction in (x, y, z) system is defined to be "Up" direction that the user prefers and is not related to the endoscope movement.

Aspect 20. The system according to aspect 19, wherein the endoscope handle (120) has a fixed handle coordinate system (x", y", z") associated with the coordinate system fixed to the guide tip, wherein the detection unit (278) is configured to identify an angle ψ between the "Up" direction (y) and the endoscope handle axis (z"), and wherein the endoscope rotation angle φ between the endoscope handle orientation (x"-y") plane and the "Up" direction projected on the x'-y' plane.

Aspect 21. An apparatus, comprising: an endoscope guide (130) extending along a longitudinal axis (Ax) and having a distal end which is bendable at an angle (θ) with respect to the longitudinal axis; an endoscope handle (120) connectable to a proximal end of the endoscope guide (130) and configured to be operated by a user to provide an orientation for the endoscope guide; imaging optics for obtaining an image of an imaging plane located at a working distance from the distal end of the endoscope guide, wherein at least part of the imaging optics is disposed within the endoscope guide and is rotatable about the longitudinal axis of the endoscope guide to direct a line of scanning light onto the imaging plane; and a processor operatively connected to the imaging optics and to the endoscope handle, the processor configured to: obtain a first angle offset value ($\varphi_1$) which is an angle difference between a first direction (535) and a second direction (533), wherein the first direction (535) is a specific direction in a display plane and the second direction (533) is a direction in which the distal tip of the endoscope guide is oriented with respect to the imaging plane; obtain a second angle offset value ($p_2$) which is an angle difference between a third direction (531) and the second direction (533), wherein the third direction (531) is a direction of a line of scanning light incident on the imaging plane, projected onto a plane perpendicular to the distal end (139), and which is to be displayed aligned with the first direction (535); generate an image (514) of the imaging plane based the detected light on a line-by-line basis; and rotate the image using the first angle offset value and the second angle offset value to correct an orientation of the image, such that the rotated image is displayed on a display device according to an image orientation that the user prefers.

Aspect 22. The apparatus according to aspect 21, wherein the processor is further configured to display on the display device one or more markers superposed on the generated image, wherein a first marker represents the image orientation that the user prefers and a second marker represents either the first angle offset value, the second angle offset value, or a combination of the first and second angle offset values.

Aspect 23. The apparatus according to aspect 21, wherein the image orientation that the user prefers is the "UP" direction of the imaging plane which is a direction opposite to the direction of gravity, and wherein the image orientation that the user prefers is not related to movement of the optical probe or the orientation of the endoscope guide.

Aspect 24. The apparatus according to aspect 21, wherein the processor obtains the first angle offset value ($\varphi_1$) by calculating an angular difference between an initial value of the rotation angle and the guide orientation, and wherein the processor obtains the second angle offset value ($\varphi_2$) by calculating a difference between a specific direction (533) for the tip (139) of the endoscope guide (130) and a direction (531) for the orientation that the user prefers.

Aspect 25. The apparatus according to aspect 21, further comprising a rotation mechanism arranged in the endoscope handle and configured to rotate the at least part of the imaging optics about the longitudinal axis of the endoscope guide and relative to the endoscope handle.

Aspect 26. The apparatus according to aspect 21, further comprising a user interface configured to control the guide orientation of the endoscope guide, wherein the user interface is provided on the endoscope handle.

Aspect 27. The apparatus according to aspect 26, wherein the user interface includes a ring dial (1302), a moving marker (1303), and an orientation indicator (1304), and wherein the user operates the ring dial to set the guide orientation of the endoscope guide to the orientation that the user prefers.

Aspect 28. A method, comprising: providing an endoscope guide (130) having a proximal end and a distal end extending along a longitudinal axis (Ax), wherein the distal end is bendable at an angle (θ) with respect to the longitudinal axis; connecting the proximal end of the endoscope guide to an endoscope handle which is configured to be operated by a user to establish an orientation for the endoscope guide; obtaining an image signal of an imaging plane located at a working distance from the distal end of the endoscope guide using imaging optics disposed within the endoscope guide, wherein at least part of the imaging optics is rotatable about the longitudinal axis of the endoscope guide to direct a line of scanning light onto the imaging plane; and obtaining a first angle offset value ($\varphi_1$) which is an angle difference between a first direction (535) and a second direction (533), wherein the first direction (535) is a specific direction in a display plane and the second direction (533) is a direction in which the distal end of the endoscope guide is oriented with respect to the imaging plane; obtaining a second angle offset value ($\varphi_2$) which is an angle difference between a third direction (531) and the second direction (533), wherein the third direction (531) is a direction of the line of scanning light incident on the imaging plane, projected onto a plane perpendicular to the distal end (139), and which is to be displayed aligned with the first direction (535); and reconstructing an image of the imaging plane using an image processor based on the obtained image signal; wherein, during the reconstructing, using one or more of the first angle offset value and the second angle offset value to rotate the image of the imaging plane such that the reconstructed image is displayed on a display device according to the first direction (535) which is the image orientation that the user prefers.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. An endoscope system, comprising:
    an endoscope;
    an endoscope guide configured to guide the endoscope through an opening thereof, the endoscope guide having a proximal portion and a distal portion with a bent or bendable distal tip configured to provide guide orientation for the endoscope;
    the endoscope comprising:
        illumination optics configured to irradiate a sample with spectrally encoded light;
        a rotation mechanism configured to rotate the illumination optics with respect to the endoscope guide so as to scan the sample with the spectrally encoded light;
        detection optics configured to detect light returned from the sample; and
    a processor operatively connected to the detection optics and the rotation mechanism, the processor configured to:
    generate an image based on a plurality of scans obtained by the detection optics during rotation of the illumination optics;
    obtain a first angle offset value between a rotation angle of the imaging optics and an angle of the guide orientation;
    obtain a second angle offset value between the angle of the guide orientation and a preferred image orientation for displaying the image; and
    rotate the image based on the first angle offset value and the second angle offset value such that the image is aligned to the preferred image orientation.

2. The system according to claim 1,
    wherein the spectrally encoded light includes a line of spectrally dispersed light,
    wherein the processor obtains the first angle value by calculating an angular difference between a specific direction in which the image is to be displayed and a direction in which the distal tip of the endoscope guide is oriented when imaging the sample; and
    wherein the processor obtains the second angle offset value by calculating an angular difference between a direction of the line of spectrally dispersed light incident on the sample and the direction in which the distal tip of the endoscope guide is oriented with respect to the sample when imaging the sample.

3. The system according to claim 1, further comprising a display apparatus,
    wherein the processor is configured to control the display apparatus to display the image in the preferred image orientation.

4. The system according to claim 3, wherein the preferred image orientation is a vertical "UP" direction of the display apparatus which is a direction opposite to the direction of gravity.

5. The system according to claim 1, wherein the preferred image orientation is independent of the rotation of the illumination optics and/or the orientation of the endoscope guide.

6. The system according to claim 1, wherein the processor obtains the first angle offset value by calculating an angular difference between an initial value of the rotation angle of the illumination optics with respect to the endoscope guide and the orientation of the endoscope guide with respect to the sample.

7. The system according to claim 1,
    wherein the illumination optics includes a spectrally encoded endoscopy (SEE) optical probe comprised of a light guiding component, a focusing component, and a diffractive component which are configured to disperse broadband light into a line of spectrally dispersed light, and
    wherein the detection optics includes a plurality of light guiding optical fibers and an optical detector configured to acquire spectral information about the spectrally dispersed light reflected from the sample.

8. The system according to claim 1, further comprising:
    an endoscope handle attached at the proximal end of the endoscope guide;
    an orientation detection unit arranged in the endoscope handle or in the endoscope guide, wherein the orientation detection unit is configured to determine an amount of pitch, roll or yaw of the endoscope handle with respect to the sample; and
    a rotation sensor configured to detect the rotation angle of the illumination optics with respect to the endoscope guide.

9. The system according to claim 1,
    wherein the processor is further configured to output to a display apparatus a plurality of markers to show how much the second angle offset value is, and
    wherein the plurality of markers are added around the image.

10. The system according to claim 9,
    wherein a first marker represents the image orientation that the user prefers and a second marker represents either the first angle offset value, the second angle offset value, or a combination of the first and second angle offset values.

11. The system according to claim 1, further comprising:
a system console including the processor and the display apparatus;
an endoscope handle connected to the endoscope guide; and
a user interface provided on the endoscope handle, or on the console, or on any another device that is connected to the handle or the console; and
wherein the user interface is configured to be operated by a user to increase or decrease the second angle offset value, and
wherein an amount to increase or decrease the second angle offset value is continuous or discrete in increments of 30 or 60 or 90 or 180 degrees.

12. The system according to claim 11,
wherein the user interface includes a ring controller around the endoscope handle, or a touchpad along a length of the endoscope handle, and wherein the user interface enables the user to choose a preset mode or value of the second angle offset value.

13. The system according to claim 11, wherein the user interface is provided on the endoscope handle, wherein the user interface includes one or more of a ring dial, a moving marker, and an orientation indicator, and wherein the user operates the ring dial to set the guide orientation of the endoscope guide to the orientation that the user prefers.

14. A method of displaying an endoscopic image in a preferred image orientation, the method comprising:
irradiating a sample with spectrally encoded light transmitted through imaging optics that rotate inside an endoscope guide, the endoscope guide having a proximal portion and a distal portion with a bent or bendable distal tip configured to provide guide orientation for the endoscope;
detecting light returned from the sample; and
generating an image based on a plurality of scans obtained by the detecting during rotation of the imaging optics;
obtaining a first angle offset value measured between a rotation angle of the imaging optics and an angle of the guide orientation;
obtaining a second angle offset value measure between the angle of the guide orientation and a preferred image orientation for displaying the image; and
rotating the image based on the first angle offset value and the second angle offset value such that the image is aligned to the preferred image orientation.

15. The method according to claim 14,
wherein irradiating the spectrally encoded light includes irradiating the sample with a line of spectrally dispersed light,
wherein obtaining the first angle value includes calculating an angular difference between a specific direction in which the image is to be displayed and a direction in which the distal tip of the endoscope guide is oriented when imaging the sample; and
wherein obtaining the second angle offset value includes calculating an angular difference between a direction in which the line of spectrally dispersed light is incident on the sample and the direction in which the distal tip of the endoscope guide is oriented with respect to an imaging plane when imaging the sample.

16. The method according to claim 14, further comprising controlling a display apparatus to display the image in the preferred image orientation.

17. The method according to claim 16, wherein the preferred image orientation is a vertical "UP" direction of the display apparatus which is a direction opposite to the direction of gravity.

18. The method according to claim 14, wherein obtaining the first angle offset value includes calculating an angular difference between an initial value of the rotation angle of the imaging optics with respect to the endoscope guide and the orientation of the endoscope guide with respect to image plane when imaging the sample.

19. The method according to claim 14, further comprising:
controlling a display apparatus to display a plurality of markers to show how much the second angle offset value is, and
displaying the plurality of markers superposed on or around the image,
wherein a first marker represents the preferred image orientation that a user prefers and a second marker represents either the first angle offset value, the second angle offset value, or a combination of the first and second angle offset values.

20. The method according to claim 14,
wherein obtaining the second angle offset value includes inputting the second angle offset value via a user interface operated by a user to increase or decrease the second angle offset value in continuous or discrete in increments,
wherein the user interface includes a ring controller around an endoscope handle connected to the endoscope guide, or a touchpad along a length of the endoscope handle, and wherein the user interface enables the user to choose a preset mode or present value for the second angle offset value.

* * * * *